US012612433B2

(12) United States Patent
Zhao et al.

(10) Patent No.: US 12,612,433 B2
(45) Date of Patent: Apr. 28, 2026

(54) HEPADNAVIRUS CAPSID PROTEIN HETERODIMERS AND VIRUS-LIKE PARTICLES

(71) Applicant: THE TRUSTEES OF INDIANA UNIVERSITY, Bloomington, IN (US)

(72) Inventors: Zhongchao Zhao, Bloomington, IN (US); Adam Zlotnick, Bloomington, IN (US)

(73) Assignee: THE TRUSTEES OF INDIANA UNIVERSITY, Bloomington, IN (US)

( * ) Notice: Subject to any disclaimer, the term of this patent is extended or adjusted under 35 U.S.C. 154(b) by 691 days.

(21) Appl. No.: 17/799,629

(22) PCT Filed: Feb. 12, 2021

(86) PCT No.: PCT/US2021/017923
§ 371 (c)(1),
(2) Date: Aug. 12, 2022

(87) PCT Pub. No.: WO2021/163538
PCT Pub. Date: Aug. 19, 2021

(65) Prior Publication Data
US 2023/0083273 A1      Mar. 16, 2023

Related U.S. Application Data

(60) Provisional application No. 62/975,916, filed on Feb. 13, 2020.

(51) Int. Cl.
*C07K 14/02*          (2006.01)
*C12N 15/63*          (2006.01)
(52) U.S. Cl.
CPC ............. *C07K 14/02* (2013.01); *C12N 15/63* (2013.01); *C12N 2730/10122* (2013.01); *C12N 2730/10123* (2013.01)
(58) Field of Classification Search
None
See application file for complete search history.

(56) References Cited

U.S. PATENT DOCUMENTS 9,950,050 B2      4/2018  Whelan et al.

FOREIGN PATENT DOCUMENTS

| WO | 2013010069 A1 | 1/2013 |
| WO | 2013036973 A2 | 3/2013 |
| WO | 2016004255 A2 | 1/2016 |

OTHER PUBLICATIONS

Kazaks et al., FEBS Letters, 2003, 549:157-162. (Year: 2003).*
Holmes, K. et al. Assembly Pathway of Hepatitis B Core Virus-like Particles from Genetically Fused Dimers. JBiol Chem 290, 16238-16245, (2015).
Kazaks A et al: "Mosaic particles formed by wild-type hepatitis B virus core protein and its deletion variants consist of both homo- and heterodimers". FEBS Letters, Elsevier, Amsterdam, NL, vol. 549, No. 1-3, (2003), pp. 157-162, XP004446882, ISSN: 0014-5793, DOI: 10.1016/s0014-5793(03)00805-6 abstract; table 1.
Lee, L. S. et al. A Molecular Breadboard: Removal and Replacement of Subunits in a Hepatitis B Virus Capsid. Protein Sci. 26(11):2170-2180. Epub Sep. 16, 2017. (2017).
Peyret, H. et al. Tandem fusion of hepatitis B core antigen allows assembly of virus-like particles in bacteria and plants with enhanced capacity to accommodate foreign proteins. PLoS One 10, e0120751 (2015).
Schlicksup, C. J. et al. Hepatitis B virus core protein allosteric modulators can distort and disrupt intact capsids. Elife 7, DOI: 10.7554/eLife.31473 (2018).
Van Eldijk, M. B. et al. Designing two self-assembly mechanisms into one viral capsid protein. J Am Chem Soc 134, 18506-18509 (2012).
Zhao, Z. et al. "Asymmetrizing an icosahedral virus capsid by hierarchical assembly of subunits with designed asymmetry", Nature Communications, vol. 12, No. 1, (2021).
Zhao, Z. et al: "Structural Differences between the Woodchuck Hepatitis Virus Core Protein in the Dimer and Capsid States Are Consistent with Entropic and Conformational Regulation of Assembly", Journal of Virology, vol. 95, No. 14, 2019.

* cited by examiner

*Primary Examiner* — Nicole Kinsey White
(74) *Attorney, Agent, or Firm* — Quarles & Brady, LLP

(57)          ABSTRACT

Embodiments described herein provide orthohepadnavirus capsid protein (Cp) heterodimers, bicistronic vectors encoding the heterodimers, and methods for producing the heterodimers. The heterodimers can be used to form mosaic virus-like particles. In certain embodiments, the heterodimers can form a hexamer, which in turn can be used to nucleate capsid formation, resulting in a Janus particle-like virus-like particle. The hexamer's can then be removed, leaving holey capsids. The capsids can be loaded with, for example, one or more polypeptides, small molecules, or a combination of polypeptides and small molecules. The holes of the holey capsids can be filled with another orthohepadnavirus heterodimer or a homodimer.

15 Claims, 13 Drawing Sheets
Specification includes a Sequence Listing.

5A

5C

5E

5B

5D

5F

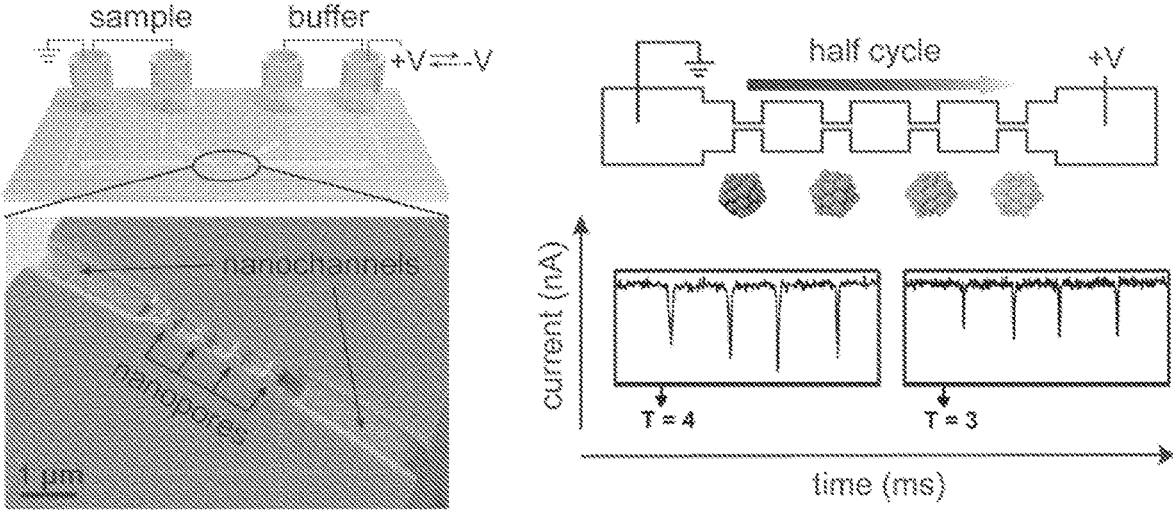
FIG. 12A                    FIG. 12B

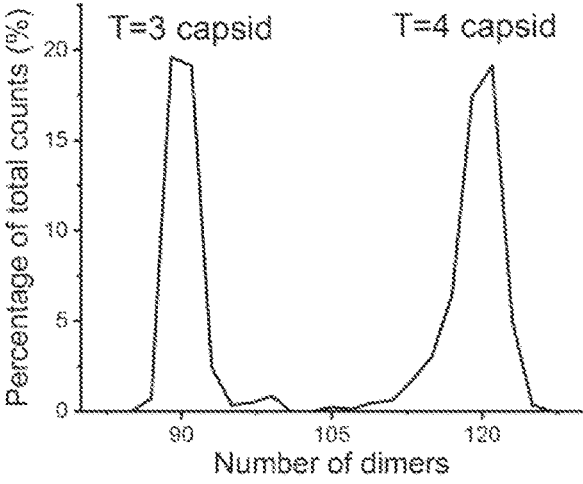
FIG. 14
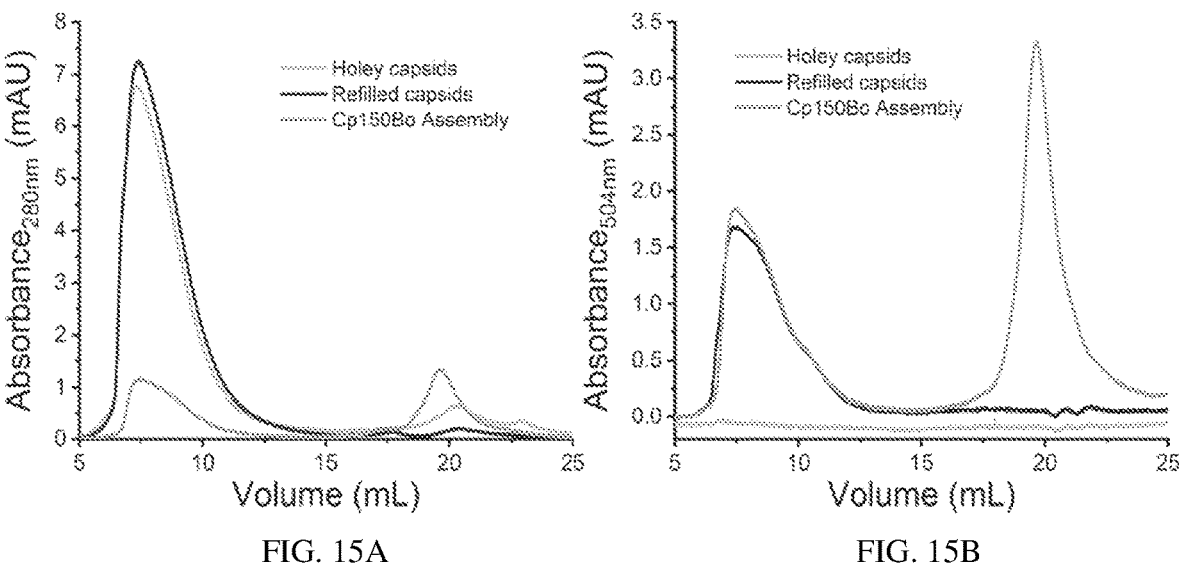
FIG. 15A                             FIG. 15B

SEQUENCE LISTING

```
<160> NUMBER OF SEQ ID NOS: 10

<210> SEQ ID NO 1
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Ala Ala Ala Leu Ala Ala Ala
1               5

<210> SEQ ID NO 2
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 2

His His His His His His
1               5

<210> SEQ ID NO 3
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Lys Asp His Leu Ile His Asn Val His Lys Glu Phe His Ala His Ala
1               5                   10                  15

His Asn Lys

<210> SEQ ID NO 4
<211> LENGTH: 450
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 4
```

-continued

```
atggacattg acccttataa agaatttgga gctactgtgg agttactctc gtttttgcct      60
tctgacttct ttccttccgt acgagatctt cttgataccg ccgcagctct gtatcgggat     120
gcattagagt ctcctgagca ctgcagccct caccatactg ccttaaggca agcaattctt     180
tgctggggag acttaatgac tctagctacc tgggtgggta ctaatttaga agatccagca     240
tctagggacc tagtagtcag ttatgtcaac actaatgtgg gcctaaagtt cagacaatta     300
ttgtggtttc acatttcttg tctcactttt ggaagagaaa cggttctaga gtatttggtg     360
tcttttggag tgtggattcg cactcctcca gcttatagac caccaaatgc ccctatcctg     420
tcgacacttc cggagactac ggttgtttag                                       450
```

```
<210> SEQ ID NO 5
<211> LENGTH: 450
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 5
```

```
atggacattg acccttataa agaatttgga gctactgtgg agttactctc gtttttgcct      60
tctgacttct ttccttccgt acgagatctt cttgataccg ccgcagctct gtatcgggat     120
gcattagagt ctcctgagca ctgcagccct caccatactg ccttaaggca agcaattctt     180
tgctggggag acttaatgac tctagctacc tgggtgggta ctaatttaga agatccagca     240
tctagggacc tagtagtcag ttatgtcaac actaatgtgg gcctaaagtt cagacaatta     300
ttgtggtttc acatttcttg tctcactttt ggaagagaaa cggttctaga gtatttggtg     360
tcttttggag tgtggattcg cactcctcca gctgcgagac caccaaatgc ccctatcctg     420
tcgacacttc cggagactac ggttgtttag                                       450
```

```
<210> SEQ ID NO 6
<211> LENGTH: 525
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (8)..(8)
<223> OTHER INFORMATION: a, c, t, g, unknown or other

<400> SEQUENCE: 6
```

```
gaattcgnga gctggataac aattcccctc tagaaataat tttgtttaac tttaagaagg      60
agatatacat atggacattg acccttataa agaatttgga gctactgtgg agttactctc     120
gtttttgcct tctgacttct ttccttccgt acgagatctt cttgataccg ccgcagctct     180
gtatcgggat gcattagagt ctcctgagca ctgcagccct caccatactg ccttaaggca     240
agcaattctt tgctggggag acttaatgac tctagctacc tgggtgggta ctaatttaga     300
agatccagca tctagggacc tagtagtcag ttatgtcaac actaatgtgg gcctaaagtt     360
cagacaatta ttgtggtttc acatttcttg tctcactttt ggaagagaaa cggttctaga     420
gtatttggtg tcttttggag tgtggattcg cactcctcca gcttatagac caccaaatgc     480
ccctatcctg tcgacacttc cggagactac ggttgtttag gatcc                     525
```

<210> SEQ ID NO 7
<211> LENGTH: 411
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (8)..(8)
<223> OTHER INFORMATION: a, c, t, g, unknown or other

<400> SEQUENCE: 7
gaattcgnga gctggataac aattcccctc tagaaataat tttgtttaac tttaagaagg      60
agatatacat ctgtggagtt actctcgttt ttgccttctg acttctttcc ttccgtacga     120
gatcttcttg ataccgccgc agctctgtat cgggatgcat tagagtctcc tgagcactgc     180
agccctcacc atactgcctt aaggcaagca attctttgct ggggagactt aatgactcta     240
gctacctggg tgggtactaa tttagaagat ccagcatcta gggacctagt agtcagttat     300
gtcaacacta atgtgggcct aaagttcaga caattattgt ggtttcacat ttcttgtctc     360 actttttggaa gagaaacggt tctagagtat ttggtgtctt ttggaggatc c             411

<210> SEQ ID NO 8
<211> LENGTH: 149
<212> TYPE: PRT
<213> ORGANISM: Hepatitis B virus

<400> SEQUENCE: 8

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ala Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
    50                  55                  60

Leu Met Thr Leu Ala Thr Trp Val Gly Thr Asn Leu Glu Asp Pro Ala
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val
145

<210> SEQ ID NO 9
<211> LENGTH: 155
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

-continued

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ala Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
        50                  55                  60

Leu Met Thr Leu Ala Thr Trp Val Gly Thr Asn Leu Glu Asp Pro Ala
65                  70                  75                  80

Ser Arg Asp Leu Val Val Ser Tyr Val Asn Thr Asn Val Gly Leu Lys
            85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
            115                 120                 125

Pro Pro Ala Tyr Arg Pro Pro Asn Ala Pro Ile Leu Ser Thr Leu Pro
        130                 135                 140

Glu Thr Thr Val Val His His His His His His
145                 150                 155

<210> SEQ ID NO 10
<211> LENGTH: 149
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ala Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
        50                  55                  60

Leu Met Thr Leu Ala Thr Trp Val Gly Thr Asn Leu Glu Asp Pro Ala
65                  70                  75                  80

Ser Arg Asp Leu Val Val Ser Tyr Val Asn Thr Asn Val Gly Leu Lys
            85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
            115                 120                 125

Pro Pro Ala Ala Arg Pro Pro Asn Ala Pro Ile Leu Ser Thr Leu Pro
        130                 135                 140

Glu Thr Thr Val Val
145
```

1

HEPADNAVIRUS CAPSID PROTEIN HETERODIMERS AND VIRUS-LIKE PARTICLES

CROSS REFERENCE TO RELATED APPLICATIONS

This application is the U.S. National Stage of PCT/US2021/017923 with international filing date of Feb. 12, 2021, which claims priority to U.S. Appl. No. 62/975,916 with filing date of Feb. 13, 2020. The content of each of the above-referenced applications is incorporated herein by reference in its entirety.

STATEMENT OF GOVERNMENT SUPPORT

This invention was made with government support under AI118933 awarded by National Institutes of Health. The government has certain rights in the invention.

SEQUENCE LISTING

The instant application contains a Sequence Listing which has been submitted via EFS-Web and is hereby incorporated by reference in its entirety. The ASCII copy, created on Feb. 12, 2021, is named IU_2020_041_02_WO_SL.txt, and is 8,737 bytes in size.

BACKGROUND

Symmetrical supramolecular protein complexes are ubiquitous in natural biological systems to compartmentalize and execute complex functions. Many groups have exploited natural systems to develop nanotechnologies for drug delivery, energy transport and information storage. Symmetrical viral capsids and their assembly are frequent platforms for these investigations. Many viral capsids have icosahedral symmetry and are assembled from a single symmetrical building block. The simplicity of viral capsids provides many advantages. However, symmetrical subunits offer little or no opportunity to control the reaction and to incorporate specific asymmetric features. This shortcoming limits development of applications that need conditional stops for information insertion and cargo loading. Methods for controlling the assembly pathway would overcome this drawback and support hierarchical assembly of a capsid.

SUMMARY

In a first example ("Example 1"), provided herein is an orthohepadnavirus capsid protein (Cp) heterodimer, including i) a first half-dimer comprising an orthohepadnavirus Cp, and ii) a second half-dimer comprising an orthohepadnavirus Cp, wherein the first half-dimer and the second half-dimer are not identical, wherein the first half-dimer and the second half-dimer are not linked by a peptide linker, and wherein the first half-dimer and the second half-dimer spontaneously dimerize with one another.

In another example ("Example 2"), further to Example 1, the first half-dimer and the second half-dimer originate from a same species of orthohepadnavirus In another example ("Example 3"), further to Example 1 or Example 2, the first half-dimer and the second half-dimer each originate from an orthohepadnavirus species selected from: hepatitis B virus (HBV), woodchuck hepatitis virus, woolly monkey hepatitis B virus, and ground squirrel hepatitis virus.

In another example ("Example 4"), further to any one of Examples 1-3, either the first half-dimer or the second half-dimer is capsid assembly-defective.

In another example ("Example 5"), further to any one of Examples 1-4, one of the first half-dimer and the second half-dimer includes a polypeptide insertion within a spike region of the first half-dimer or the second half-dimer, the polypeptide insertion being selected from: an exogenous polypeptide epitope, an exogenous immunogenic polypeptide, an exogenous therapeutic polypeptide, an exogenous ligand polypeptide, a capsid self-assembly or disassembly regulating polypeptide sequence, and an exogenous catalytic polypeptide.

In another example ("Example 6"), further to any one of Examples 1-5, one or both of the first half-dimer and the second half-dimer includes a polypeptide linked to a C-terminus of the first half-dimer or second half-dimer, the linked polypeptide being selected from: a capsid self-assembly or disassembly regulating polypeptide sequence, an exogenous catalytic polypeptide, an exogenous affinity tag polypeptide, a C-terminal cysteine, an exogenous elastin-like polypeptide, an exogenous leucine zipper polypeptide, an exogenous catalytic polypeptide, or an exogenous fluorescent polypeptide.

In another example ("Example 7"), further to any one of Examples 1-6, either the first half-dimer or the second half-dimer includes a polyhistidine tag or a histidine affinity tag.

In another example ("Example 8"), further to any one of Examples 1-7, the first half-dimer includes a first hepatitis B virus (HBV) Cp, and the second half-dimer includes a second HBV Cp.

In another example ("Example 9"), further to any one of Examples 1-8, either the first half-dimer or the second half-dimer includes an HBV Cp selected from the group of: HBV Cp140; HBV Cp149; HBV Cp149-3CA; HBV Cp149-S106A; HBV Cp149-G123A; HBV Cp149-V124A; HBV Cp149-V124W; HBV Cp149-V124C; HBV Cp149-T128A; HBV Cp149-Y132A; HBV Cp150; HBV Cp150-V124C; and HBV Cp183.

In another example ("Example 10"), further to any one of Examples 1-9, either the first half-dimer or the second half-dimer includes one of: HBV Cp149-S106A; HBV Cp149-G123A; HBV Cp149-V124A; HBV Cp149-V124C; HBV Cp149-T128A; or HBV Cp149-Y132A.

In another example ("Example 11"), further to any one of Examples 1-10, the first half-dimer includes HBV Cp149, and the second half-dimer includes HBV Cp149-Y132A.

In another example ("Example 12"), provided herein is a bicistronic vector encoding an orthohepadnavirus capsid protein (Cp) heterodimer according to any one of Examples 1-11.

In another example ("Example 13"), further to Example 12, the bicistronic vector includes a promoter followed by a first ribosomal binding site sequence associated with a first nucleotide sequence that encodes the first half-dimer, and a second ribosomal binding site sequence associated with a second nucleotide sequence that encodes the second half-dimer.

In another example ("Example 14"), provided herein is a method for making a orthohepadnavirus capsid protein (Cp) heterodimer, comprising: introducing the bicistronic vector of Example 11 or Example 12 into a cell; incubating the cell comprising the bicistronic vector for a time sufficient for the cell to express the first half-dimer and the second-half dimer from the bicistronic vector; and recovering and purifying a heterodimer consisting of the first half-dimer and the second half-dimer.

In another example ("Example 15"), further to Example 14, at least one of the first half-dimer and the second half-dimer includes an affinity tag peptide sequence and recovery and purification of the heterodimer includes affinity purification.

In another example ("Example 16"), further to Example 14, the affinity tag peptide sequence is a polyhistidine tag.

In another example ("Example 17"), further to Example 14, the cell is a cell selected from: an *Escherichia coli* cell; a *Corynebacterium* spp. cell; a *Pseudomonas fluorescens* cell; a *Saccharomyces cerevisiae* cell; and a *Pichia pastoris* cell.

In another example, ("Example 18), further to any one of Examples 14-17, the method further includes attaching one or more external moieties to the orthohepadnavirus Cp heterodimer.

In another example ("Example 19"), further to Example 18, the one or more external moieties are selected from an exogenous polypeptide, a dye, and a fluorophore.

In another example ("Example 20"), further to Example 18 or Example 19, the one or more external moieties are attached to a C-terminal cysteine residue of the first half-dimer or the second half-dimer.

In another example ("Example 21"), further to any one of Examples 18-20, the at least one of the first half-dimer and the second half-dimer includes a cysteine residue a spike tip of the first half-dimer or the second half-dimer, and the one or more external moieties are attached via the cysteine residue at the spike tip of the first half-dimer or the second half-dimer.

In another example ("Example 22"), provided herein is a viral capsid protein hexamer comprising six orthohepadnavirus capsid protein (Cp) heterodimers according to any one of Examples 1-11.

In another example ("Example 23"), further Example 22, the first half-dimer or the second half-dimer of each one of the six orthohepadnavirus Cp heterodimers includes a polyhistidine tag, and the viral capsid hexamer further includes metal ions selected from $Ni^{2+}$, $Co^{2+}$, $Cu^{2+}$, and $Zn^{2+}$.

In another example ("Example 24"), further to Example 22, the first half-dimer or the second half-dimer of each one of the six orthohepadnavirus Cp heterodimers includes an elastin-like polypeptide configured to aggregate the orthohepadnavirus Cp heterodimers into a hexamer.

In another example ("Example 25"), further to Example 22, the first half-dimer or the second half-dimer of each one of the six orthohepadnavirus Cp heterodimers comprises a leucine zipper polypeptide configured to aggregate the hepadnavirus Cp heterodimers into a hexamer.

In another example ("Example 26"), provided herein is a method for making a viral capsid protein hexamer, including incubating a plurality of orthohepadnavirus capsid protein (Cp) heterodimers according any one of Examples 1-11 with metal ions selected from Ni2+, Co2+, Cu2+, and Zn2+ in a low ionic strength buffer, wherein the first half-dimer or the second half-dimer of each heterodimer of the plurality of orthohepadnavirus Cp heterodimers includes a polyhistidine tag.

In another example ("Example 27"), further to Example 26, the low ionic strength buffer has an ionic strength of about 100 μM or less.

In another example ("Example 28"), further to Example 26 or Example 27, the low ionic strength buffer includes about 50 mM HEPES and no NaCl.

In another example ("Example 29"), provided herein is a virus-like particle (VLP) including a plurality of orthohepadnavirus capsid protein (Cp) heterodimers according to any one of Examples 1-11.

In another example ("Example 30"), further to Example 29, further including a plurality of orthohepadnavirus Cp homodimers.

In another example ("Example 31"), further to Example 29 or Example 30, the plurality of orthohepadnavirus Cp heterodimers includes two or more different orthohepadnavirus Cp heterodimers.

In another example ("Example 32"), further to Example 26, the two or more different orthohepadnavirus Cp heterodimers differ in i) the orthohepadnavirus Cp forming either or both of the first half-dimer and the second half-dimer, ii) the polypeptide insertion, iii) the linked polypeptide, or iv) any combination of the orthohepadnavirus Cp forming either or both of the first half-dimer and the second half-dimer, the polypeptide insertion, and the linked polypeptide.

In another example ("Example 33"), further to Example 31 or Example 32, wherein the plurality of orthohepadnavirus Cp heterodimers include a first population of heterodimers comprising a first polypeptide insertion, and a second population of heterodimers comprising a second polypeptide insertion, wherein the first exogenous polypeptide and the second exogenous polypeptide are not identical.

In another example ("Example 34"), further to any one of Examples 30-33, the plurality of orthohepadnavirus Cp homodimers includes one or more of: HBV Cp140; HBV Cp149; HBV Cp149-3CA; HBV Cp150; and HBV Cp183.

In another example ("Example 35"), further to any one of Examples 29-34, the VLP includes at least one viral capsid protein hexamer according to any one of Examples 22-25.

In another example ("Example 36"), further to any one of Examples 29-35, one or more nucleic acid sequences, one or more polypeptides, one or more small molecules, or any combination thereof is contained within the VLP.

In another example ("Example 37"), provided herein is a method for making a virus-like particle (VLP), comprising incubating a plurality of viral capsid protein hexamers according to any one of Examples 22-25 with i) a plurality of orthohepadnavirus capsid protein (Cp) heterodimers according to any one of Examples 1-1, ii) a plurality of orthohepadnavirus homodimers, or iii) a combination of a plurality of orthohepadnavirus capsid protein (Cp) heterodimers according to any one of Examples 1-11 and a plurality of orthohepadnavirus homodimers.

In another example ("Example 38"), further to Example 37, the method includes disassembling the plurality of viral capsid protein hexamers following formation of a VLP to produce a holey VLP.

In another example ("Example 39"), further to Example 38, the method includes loading the holey VLP with one or more nucleic acid sequences, one or more polypeptides, one or more small molecules, or any combination thereof.

In another example ("Example 40"), further to Example 38 or Example 39, the method includes filling the holes of the holey VLP with i) orthohepadnavirus CP heterodimers according to any one of Examples 1-11, ii) orthohepadnavirus homodimers, or iii) a combination of orthohepadnavirus CP heterodimers according to any one of Examples 1-11 and orthohepadnavirus homodimers, wherein if the VLP is it be filled according to Example 39, the holes of the holey VLP are filled after the holey VLP is loaded.

In another example ("Example 41"), further to any one of Example 37-40, wherein the plurality of orthohepadnavirus Cp heterodimers includes two or more populations of orthohepadnavirus Cp heterodimers, wherein heterodimers of the two or more populations of orthohepadnavirus Cp heterodimers are not identical.

In another example ("Example 42"), further to Example 41, the one or more populations of orthohepadnavirus Cp heterodimers each include a different polypeptide insertion; or one of the one or more populations of orthohepadnavirus Cp heterodimers does not include a polypeptide insertion, and each additional population of orthohepadnavirus Cp heterodimers each include a different polypeptide insertion.

In another example ("Example 43"), further to any one of Examples 37-42, the plurality of viral capsid protein hexamers include hexamers consisting of six HBV Cp149HisCp149Y132A heterodimers and a metal ion selected from Ni2+, Co2+, Cu2+, and Zn2+.

In another example ("Example 44"), further to any one of Examples 37-43, viral capsid protein hexamers of the plurality of viral capsid protein hexamers include i) orthohepadnavirus Cp heterodimers comprising a polyhistidine tag, and ii) a metal ion selected from Ni2+, Co2+, Cu2+, and Zn2+, and wherein the plurality of viral capsid protein hexamers are disassembled using ethylenediaminetetraacetic acid (EDTA).

In another example ("Example 45"), further to any one of Examples 37-44, the plurality of orthohepadnavirus Cp homodimers one or more of: HBV Cp140; HBV Cp149; HBV Cp149-3CA; HBV Cp150; and HBV Cp183.

In another example ("Example 46"), provided herein is a method for making a virus-like particle (VLP), comprising incubating i) a plurality of orthohepadnavirus capsid protein (Cp) heterodimers according to any one of Examples 1-11, or ii) a combination of a plurality of orthohepadnavirus capsid protein (Cp) heterodimers according to any one of Examples 1-11 and a plurality of orthohepadnavirus homodimers.

In another example ("Example 47"), further to Example 47, the one or more populations of orthohepadnavirus Cp heterodimers each include a different polypeptide insertion; or one of the one or more populations of orthohepadnavirus Cp heterodimers does not include a polypeptide insertion, and each additional population of orthohepadnavirus Cp heterodimers each include a different polypeptide insertion.

BRIEF DESCRIPTION OF THE DRAWINGS

The following drawings form part of the present specification and are included to further demonstrate certain embodiments. Some embodiments may be better understood by reference to one or more of these drawings alone or in combination with the detailed description of specific embodiments presented.

FIG. 12A is a schematic (top) and a scanning electron micrograph (bottom) of a nanofluidic device used for multicycle resistive-pulse sensing.

FIG. 12B is a schematic illustrating a multicycle resistive-pulse sensing experiment according to certain embodiments.

FIG. 14 depicts a typical resistive pulse sensing histogram of a mixture of purified T=3 and purified T=4 capsids.

FIGS. 15A and 15B depict chromatographs 280 nm (FIG. 15A) and 504 nm (FIG. 15B), showing BODIPY co-eluting with refilled capsids and Cp150Bo capsids

DETAILED DESCRIPTION

Figure 1:
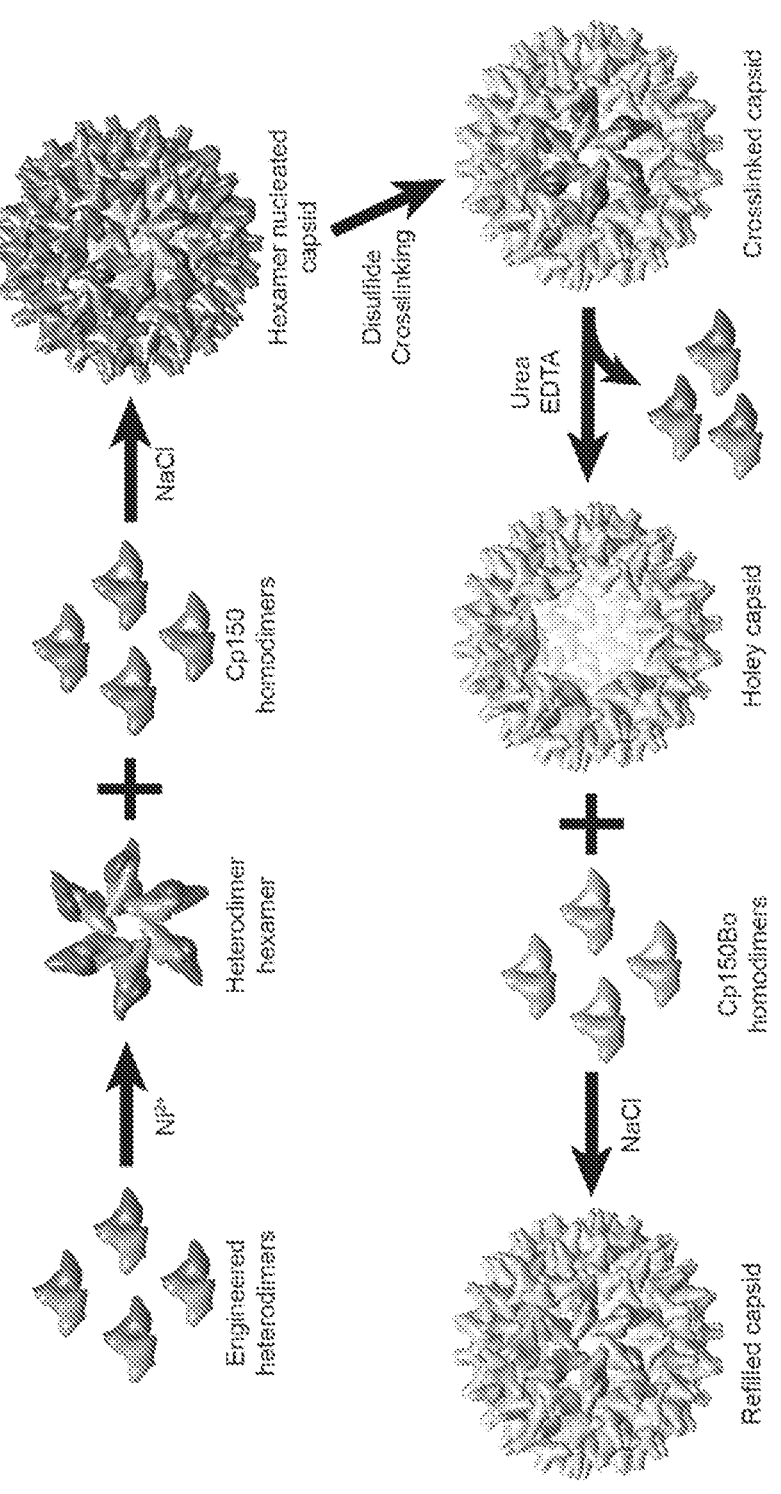
FIG. 1 is a schematic depicting the hierarchical assembly of an HBV capsid analog starting with an asymmetric dimeric (i.e., heterodimeric) subunit according to certain embodiments.

For the purposes of promoting an understanding of the principles of the novel technology, reference will now be made to various embodiments of the compositions, methods of making, and methods of use thereof, and specific language will be used to describe the same. It will nevertheless be understood that no limitation of the scope of the novel technology is thereby intended, such alterations, modifications, and further applications of the principles of the novel technology being contemplated as would normally occur to one skilled in the art to which the novel technology relates are within the scope of this disclosure and the claims.

Unless otherwise indicated in the context a term is used, the terms will have the following meanings as utilized herein.

The term 'about' refers to a range of values plus or minus 10 percent, e.g., about 1.0 encompasses values from 0.9 to 1.1.

Although capsid assembly has nucleation and elongation phases, there are no discrete stopping points for manipulation and modification of specific intermediates. As described herein, Hepatitis B Virus (HBV) capsid assembly is used as a model system and demonstrates an effective approach to break the spontaneous assembly into addressable steps. HBV capsid dimeric subunits can assemble two species of capsids, T=3 capsid with 90 dimers and T=4 capsid with 120 dimers. T=4 capsid is the predominant species and the capsid within infectious virions. HBV dimers interact when the end of the "contact helix" of one dimer fits into a groove formed by the contact helix of subunit from an adjacent dimer (note the hexamer in FIG. 1). Of course, a dimer has two contact helices at either end (see FIG. 2A). In concept, both monomers can be engineered differently, leading to a heterodimer for which each monomer can only assemble with other dimers in response to a specific condition. One extreme example would be a heterodimer with an assembly-active monomer and an assembly-incompetent monomer.

Described herein is a platform and some basic manipulations for controlled assembly. A heterodimer was designed and used to generate small complexes that, in turn, can nucleate assembly of a capsid. The co-assembled capsid has two discrete and addressable patches, a heterodimer patch and a homodimer patch, analogous to a Janus particle. By virtue of a distinct hydrophobic patch, Janus particles can be driven to assemble into larger supramolecular structures. Here, the chemically distinct nature of the two patches results in the ability to control further modification, disassembly, and reassembly.

Embodiments described herein provide orthohepadnavirus capsid protein (Cp) heterodimers, bicistronic vectors encoding the heterodimers, and methods for producing the heterodimers. The heterodimers can be used to form mosaic virus-like particles. In certain embodiments, the heterodimers can form a hexamer, which in turn can be used to nucleate capsid formation, resulting in a Janus particle-like virus-like particle. The hexamer's can then be removed, leaving holey capsids. The capsids can be loaded with, for example, one or more polypeptides, small molecules, or a combination of polypeptides and small molecules. The holes of the holey capsids can be filled with another orthohepadnavirus heterodimer or a homodimer.

Heterodimeric Capsid Proteins

Symmetrical protein complexes, such as those of HBV, are ubiquitous in biology. Many have been reengineered for chemical and medical applications. Viral capsids (including HBV) and their assembly are frequent platforms for these investigations. A means to create asymmetric capsids may expand applications. As described herein, such means begin with a heterodimer.

Hepatitis B virus (HBV) capsid proteins (Cps) assemble around the pregenomic RNA (pgRNA) and viral reverse transcriptase (P). pgRNA is then reverse transcribed to double-stranded DNA (dsDNA) within the capsid. The Cp assembly domain, which forms the shell of the capsid, regulates assembly kinetics and capsid stability. The Cp, via its nucleic acid-binding C-terminal domain, also affects nucleic acid organization. The HBV capsid is in T=4 or T=3 icosahedral symmetry, with T=4 capsids accounting for a major population in the natural HBV pool.

The basic building block of HBV capsid is Cp, which is 183 amino acids (aa) in length, and exists as a homodimer in solution. The N-terminal 149 aa are the assembly domain (Cp149). The C-terminus (amino acids 150 to 183) are enriched in arginine and have nucleic acid-binding properties. HBV capsid assembly has been studied extensively in vitro using Cp149. Weak protein-protein interactions at the interdimer interface drive capsid assembly and maintain capsid stability.

HBV is described and provided herein as a model system, although the materials and methods describe can be readily adapted by those of skill in the art to other orthohepadnavirus capsid proteins. For example, while HBV is provided as a model system, similar results have been obtained with woodchuck hepatitis virus.

Heterodimers generally include a first half-dimer and a second half-dimer, wherein the first half-dimer and the second half-dimer are not identical, and the first half-dimer and the second half-dimer spontaneously dimerize with one another. The first half dimer and the second half-dimer can differ by any aspect described herein, including but not limited to the half-dimer backbone, a polypeptide insertion, or a C-terminal tag or other C-terminal exogenous polypeptide.

Figure 16:
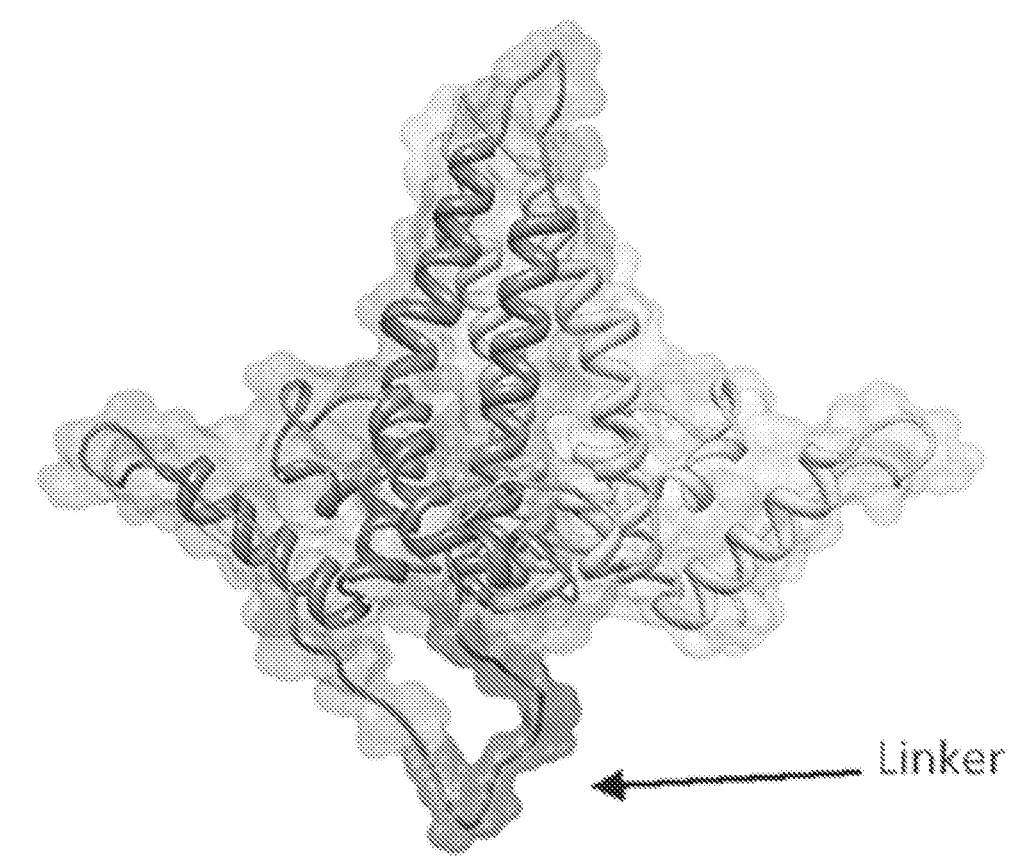
FIG. 16 depicts a tandem dimer including a polypeptide linker between the two half-dimers.

The first and second half-dimers are not linked by a polypeptide linker. Others have attempted to generate tandem dimers, wherein two half-dimers of HBV Cp are linked via a polypeptide linker (see, e.g., U.S. Pat. No. 9,950,050). A representative example of a tandem HBV dimer is illustrated by FIG. 16. In the hands of the inventors, the tandem arrangement resulted in low yield and produced many aggregates. This was due to the linkage between the two monomers, which led to misfolding. As described herein, such a linkage is not required in order to produce hepadnavirus heterodimers.

Generally, the first half-dimer and the second half-dimer are derived from the same species of orthohepadnavirus. The first half-dimer and the second half-dimer can be from an orthohepadnavirus species. Examples of orthohepadnavirus species include HBV, woodchuck hepatitis virus, woolly monkey hepatitis B virus, and ground squirrel hepatitis virus. In certain embodiments, both the first half-dimer and the second half-dimer are HBV Cps.

Several HBV Cp variants are known in the art, each with their own unique properties. The first half-dimer and the second half-dimer can have the same 'backbone' (i.e., based on the same variant), or can be different. Wherein the same variant forms the backbone for each of the first half-dimer and the second half-dimer, some other aspect of the half-dimers differentiates the two. For example, the first half-dimer might include a polyhistidine tag, while the second half-dimer includes an exogenous polypeptide inserted in the half-dimer's spike tip. Each of the first half-dimer and the second-half dimer can be selected from the group of: HBV Cp183; HBV Cp140; HBV Cp149; HBV Cp149-3CA; HBV Cp149-3CA-E77C; HBV Cp149-E77K; HBV Cp149-K7R, E77K,K97R; HBV Cp150; and Cp150-V124C. The characteristics of these Cps are summarized in Tables 1 and 2.

Either the first half-dimer or the second half-dimer can be assembly-defective. That is, one of the two half-dimers has a diminished capacity for viral capsid assembly relative to wild-type. Alternatively, either the first half-dimer or the second half-dimer can have an enhanced capacity for viral capsid assembly relative to wild-type. A heterodimer including a half-dimer with altered assembly characteristics provides means for regulating assembly. For example, a heterodimer can have an assembly active half-dimer and an assembly defective half-dimer. The assembly active half-dimer can assemble in response to ionic strength, while the assembly defective half-dimer inhibits assembly. In some embodiments, the assembly defective half-dimer can still co-assemble with wildtype homodimers. Examples of HBV half-dimers having altered assembly are known in the art, and include HBV Cp149-S106A; HBV Cp149-G123A; HBV Cp149-V124A; HBV Cp149-V124C; HBV Cp149-T128A; or HBV Cp149-Y132A. Table 1 provides a summary of these and other HBV half-dimers.

TABLE 1

Mutants and Variants of HBV Cp.

| Variant | mutations | features |
|---|---|---|
| Cp183 | | Full-length core protein. Carries an arginine-rich C-terminal domain that can bind nucleic acid, bind cellular importin proteins, and can act as a cell permeating peptide. |
| Cp149 | | Assembly domain, forms >90% T = 4 capsid |
| Cp140 | | truncated assembly domain. Higher proportion of T = 3 capsids (~50%), stronger association. |
| Cp149-3CA | Cp149-C48A, C61A, C107A | Cp devoid of all cysteines, a chemically addressable amino acid. |
| Cp150 | Cp149-C48A, C61A, C107A, C150 | Cp with a single C-terminal cysteine. C150 can be modified with maleimide and other specific chemistries. When not blocked, C150 can crosslink and stabilize capsids. |
| Cp149-Y132A | | Assembly incompetent. |
| Cp149-G123A | | Assembly incompetent. |
| Cp149-V124A | | Severe assembly attenuation. |
| Cp149-T128A | | Modest assembly attenuation. |
| Cp149-S106A | | Modest assembly attenuation. |
| Cp149-V124W | | Enhanced assembly. |
| Cp149-V124C | | Modest assembly attenuation. C124 can be modified with a bulky ligand prior to assembly to block assembly. C124 modified after assembly activates disassembly. |
| Cp150-V124C | Cp149-C48A, C61A, C107A, V124C, C150 | Two active cysteines. In a capsid, C150 will spontaneously oxidize to form C150-C150 disulfides, covalently crosslinking the capsid. C124 modified with a bulky substituent (e.g. fluorescein) makes the capsid metastable so that it dissociates when exposed to reducing agents. |

TABLE 2

HBV Cp added-function variants.

| Variant | Features |
|---|---|
| Cp149-3CA-E77C | Inserts an accessible cysteine into the spike tip that is easily addressed using maleimide and other chemistry |

TABLE 2-continued

HBV Cp added-function variants.

| Variant | Features |
|---|---|
| Cp149-E77K | Inserts an accessible lysine into the spike tip that is easily addressed using NHS chemistry and isothiocyante chemistry |
| Cp149-K7R, E77K, K97R | Inserts an accessible lysine into the spike tip while replacing the two other lysines in Cp with arginine, which has the same charge but is not modified by NHS or ITC chemistry |
| Cp149-ΔP79, A80 | Insertion site. Replace P79, A80 with a protein[15] |

In particular embodiments, the first half-dimer has an HBV Cp149 backbone (SEQ ID NO: 8) or an HBV Cp149-6×His backbone (SEQ ID NO: 9), and the second half-dimer has an HBV Cp149-Y132A backbone (SEQ ID NO: 10).

It will be recognized by those of skill in the art that mutations to the various Cp backbones described herein can be made. Such mutations may or may not affect, for example, the ability of the Cp backbone to assemble into capsids. Such mutations and the resulting variants are also within the scope of the instant disclosure.

The first-half-dimer or the second half-dimer can include a polypeptide insertion within its spike region. The polypeptide insertion can be, for example, an exogenous polypeptide epitope, an exogenous immunogenic polypeptide, an exogenous therapeutic polypeptide, an exogenous ligand polypeptide, a capsid self-assembly or disassembly regulating polypeptide sequence, and an exogenous catalytic polypeptide. Having the exogenous polypeptide insertion on only one of the first half-dimer or second half-dimer minimizes steric hinderance that would result if the dimer were homodimeric (or heterodimeric) with each half-dimer having a polypeptide insertion within its spike region. Such steric hindrance could prevent or otherwise negatively affect dimerization and/or capsid assembly.

The exogenous polypeptide to be inserted in the spike region of a half-dimer can be any desired exogenous polypeptide. Examples include epitopes, immunogenic polypeptides, therapeutic polypeptides, ligands, capsid self-assembly or disassembly regulating polypeptides, and catalytic polypeptides. Epitopes can be included when a capsid or virus-like particle (VLP) including heterodimers including the epitope are to be used in in vitro diagnostics to detect the presence of antibody in a sample. Such VLPs can also be used as a artificial antigen presenting cells. Immunogenic polypeptides include any antigen or antigen fragment capable of eliciting an immune response in a subject. VLPs including the immunogenic polypeptides can be used as a vaccine. The inclusion of ligands can direct VLPs to specific target sites rich in one or more target receptors. Catalytic polypeptides (i.e., catalytic domains of enzymes) can be included to aid in in vitro diagnostics, or can be selected to function in vivo.

In some embodiments, monomeric streptavidin can be inserted in the spike region of one half-dimer of a heterodimer. VLPs bearing monomeric streptavidin can be used in the purification or detections of biotin-tagged biomolecules. Alternatively, such VLPs can themselves be easily purified due to the presence of streptavidin. VLPs including monomeric streptavidin can also be in pre-targeted immunotherapy, where the VLPs are conjugated to a monoclonal antibody against cancer cell-specific antigens. Radiolabeled biotin then targets radiation only to the cancerous cells, and given the high number of monomeric streptavidin polypeptides associated with each VLP, the VLPs provide for amplification of radiation.

In other embodiments, the SARS-CoV2 N-protein N-terminal domain can be inserted in the spike region of on half-dimer of a heterodimer.

The two α-helices that make up the HBV Cp spike region are not symmetrical and so the resulting spike tip does not point completely vertically from a VLP, but is slightly offset. Any inserted exogenous polypeptide may thus lie parallel to the VLP, rather than at a right angle. This could possibly lead to steric hindrance. The half-dimer that is to include the inserted polypeptide can include an inserted sequence which acts to "balance" the α-helices by adding an extra turn or turns to the first helix of HBV Cp (amino acids 50 to 73). This results in the presentation of an inserted polypeptide in a perpendicular orientation relative to the VLP. This "balancing sequence" can be from 3 to 12 amino acids (e.g. 3, 5 or 7 amino acids). These amino acids can be uncharged amino acids such as alanine, leucine, serine and threonine. The inserted sequence can be AAALAAA (SEQ ID NO: 1). The insertion can be at a site between amino acids 50 and 75 of HBV Cp, for example at a site between residues 60 and 75 or residues 70 and 73.

The exogenous polypeptide can be inserted at P79/A80 of HBV Cp, wherein P79 and A80 amino acids are replaced with the exogenous polypeptide.

One or both of the first half-dimer and the second half-dimer can include a polypeptide linked to the half-dimer's C-terminus. The polypeptide linked to the half-dimer's C-terminus can be in addition to an exogenous polypeptide insertion at the half-dimer's spike region, or the half-dimer's spike region can be free of an exogenous polypeptide insertion. The polypeptide linked to a half-dimer's C-terminus can be a capsid self-assembly or disassembly regulating polypeptide sequence, and an exogenous catalytic polypeptide, an exogenous affinity tag polypeptide, a C-terminal cysteine, an exogenous elastin-like polypeptide, an exogenous leucine zipper polypeptide, an exogenous catalytic polypeptide, or an exogenous fluorescent polypeptide. When half-dimers including a polypeptide linked to its C-terminus are assembled into capsids (i.e., VLPs), the linked C-terminal polypeptide will be located withing the capsid. This allows for unique internal chemistries and capsid characteristics.

The linked C-terminal polypeptide can be an exogenous affinity tag polypeptide. Examples include polyhistidine (His6x; SEQ ID NO: 2) and histidine affinity tag (KDH-LIHNVHKEFHAHAHNK; SEQ ID NO: 3). In certain embodiments, the linked C-terminal polypeptide is polyhistidine. Polyhistidine has several beneficial characteristics in that it not only provides for simple Cp heterodimer purification, but also facilitates formation of Cp heterodimer multimers, as provided herein. As a purification tag, Cp heterodimers including the polyhistidine tag can be purified by methods known in the art. For example, Cp heterodimers including a polyhistidine tag on at least one of its half-dimers can be affinity purified utilizing an affinity resin or beads including bound divalent nickel or cobalt ions to capture the target heterodimers. The resin or beads are then washed with phosphate buffer to remove non-specific binding, followed by elution of the target heterodimers using an appropriate buffer. As discussed in further detail below, the polyhistidine tag, through its interactions with divalent metal ions, also facilitates aggregation of several heterodimers into a multimer of heterodimers, such as hexamers.

Catalyzed reactions can be carried out within an assembled capsid by linking an exogenous catalytic polypeptide to the C-terminus of one half-dimer of a heterodimer. The exogenous catalytic polypeptide can be, for example, an enzyme's catalytic domain.

Exogenous elastin-like polypeptides or leucine zipper polypeptides can be linked to the C-terminus of one half-dimer of a heterodimer. Elastin-like polypeptides and leucine zippers are known mediate aggregation, and can be engineered to support and/or control capsid assembly.

Exogenous fluorescent polypeptides can be linked to the C-terminus of one half-dimer of a heterodimer. Such fluorescent polypeptides can allow for monitoring of capsid assembly involving the fluorescently labelled heterodimers.

In certain embodiments, a cysteine residue is included at the C-terminus of one half-dimer of a heterodimer, as in HBV Cp150. This modification provides for a polypeptide to be directly linked to the C-terminus of the half-dimer via a disulfide bond. Methods for linking proteins via cysteine residues are known in the art.

The polypeptide linked to the C-terminus of a half-dimer can either form an integral part of the half-dimer (i.e., the Cp half-dimer and the polypeptide linked to the C-terminus are expressed as a single protein), or a desired polypeptide can be linked to the C-terminus of the half-dimer following production of the half-dimer (e.g., via two cysteine residues).

It will be apparent to those skilled in the art that a wide variety of orthohepadnavirus Cp heterodimers can be generated in accordance with the present disclosure. For example, many different exogenous polypeptides can be inserted in the spike region of one half-dimer of a heterodimer. As further described below, this allows for the formation of mosaic VLPs presenting a plurality of exogenous polypeptides on their surface.

Nucleic Acids and Expression Vectors

Also provided are nucleic acid molecules that encode the orthohepadnavirus capsid protein heterodimers disclosed herein. Nucleic acid sequences that have been optimized for expression in a chosen expression system are also disclosed. The expression system can be based on, for example, *Escherichia coli*, *Corynebacterium* spp., *Pseudomonas fluorescens*, *Saccharomyces cerevisiae*, or *Pichia pastoris*.

The nucleic acid sequence encoding the Cp heterodimer can be included in an expression cassette for use in the chose expression system. Expression cassettes generally include a promoter at the 5' end of the cassette, upstream of the Cp heterodimer-encoding nucleic acid sequence. Untranslated DNA at the 5' end of the coding sequence can include a promoter region with multiple promoter and/or enhancer elements operably linked to the nucleic acid sequence to provide for initiation of transcription. Nucleic acid sequences encoding the first half-dimer and the second half-dimer are arranged to provide for the two half-dimers being expressed without being linked together. In this regard, the nucleic acid sequence encoding each half-dimer can be associated with its own ribosomal binding sequence. This allows for separate expression of each half dimer. As dimerization occurs very rapidly, Cp homodimers are not detectable following expression. This eliminates any need for a polypeptide linker between the two half-dimers to ensure dimerization.

The expression system can be *E. coli*, and the optimized nucleic acid sequence (i.e., cDNA) for HBV Cp149 can be SEQ ID NO: 4, and the optimized nucleic acid sequence for HBV Cp149$_{Y132A}$ can be SEQ ID NO: 5.

The nucleic acid sequence encoding the Cp heterodimer (e.g., an expression cassette disclosed herein) can be included in an expression vector expressible in the chosen expression system. In this regard, recombinant expression vectors are provided comprising a nucleic acid sequence that encodes a Cp heterodimer of the disclosure. The term "recombinant expression vector" refers to a genetically modified oligonucleotide or polynucleotide construct that permits the expression of the Cp heterodimer by a host cell. Recombinant expression vectors include a suitable vector backbone for use in transforming or transfecting host cells of a chosen expression system. Suitable vector backbones for various expression systems are known and include plasmids and viruses. Recombinant expression vectors can be prepared using recombinant DNA techniques described and known in the art, as demonstrated in the Experimental Examples.

The recombinant expression vector can include a native or non-native promoter operably linked to the nucleic acid sequence encoding the Cp heterodimer. The recombinant expression vector can include regulatory sequences, such as transcription and translation initiation and termination codons, which are specific to the type of host cell (e.g., *E. coli*) into which the vector is to be introduced, as appropriate. The recombinant expression vector can also include restriction sites to facilitate cloning.

The recombinant expression vector can include one or more marker genes, which allow for selection of transformed or transfected host cells. Marker genes include biocide resistance, e.g., resistance to antibiotics, heavy metals, etc., complementation in an auxotrophic host to provide prototrophy, and the like.

Also provided are host cells including an expression cassette or expression vector described herein. The term "host cell" refers to any type of cell that can contain and express an expression cassette or expression vector described herein. The host cell can be a eukaryotic cell, e.g., yeast, plant, animal, fungi, or algae, or can be a prokaryotic cell, e.g., bacteria or protozoa. The host cell can be an adherent cell or a suspended cell, i.e., a cell that grows in suspension. Suitable host cells include, for example, *E. coli* cells, *Corynebacterium* spp. cells, *Pseudomonas fluorescens* cells, *Saccharomyces cerevisiae* cells; and *Pichia pastoris* cells.

Also provided is a population of host cells. The population of host cells can be a clonal population of cells, in which all cells of the population are clones of a single host cell including a recombinant expression vector.

The Cp heterodimer fusion polypeptide can be isolated and/or purified from a host cell or a population of host cells. Generally, an expression vector provided herein (i.e., a bicistronic vector) is introduced into a host cell. The host cell including the bicistronic vector is incubated for a time sufficient for the host cell to express both the first half-dimer and the second half-dimer from the bicistronic vector. The first half-dimer and the second half-dimer then spontaneously dimerize, and the resulting heterodimer is recovered. Recovery and purification can be facilitated by, for example, inclusion of an affinity tag (e.g., 6×His (SEQ ID NO: 2)) at the C-terminus of either the first half-dimer or the second half-dimer.

Following recovery and purification, external moieties can be linked to the Cp heterodimer by, for example, a cysteine-cysteine linkage. Possible external moieties include an exogenous polypeptide, a dye, and a fluorophore. The external moiety can be linked to a C-terminal cysteine residue (e.g., the C-terminal cysteine of HBV Cp150), or to any other cysteine residue. For example, HBV Cp150 includes a cysteine residue at its C-terminus; HBV Cp149 includes accessible cysteine residues at amino acid positions 48, 61, and 107; and HBV Cp149-3CA-E77C has an accessible cysteine introduced into the half-dimer's spike tip that is easily addressed using maleimide and other chemistry, while the cysteine residues at amino acid positions 48, 61, and 107 are each substituted by alanine.

Exogenous polypeptides can be, for example, an exogenous polypeptide epitope, an exogenous immunogenic polypeptide, an exogenous therapeutic polypeptide, an exogenous ligand polypeptide, a capsid self-assembly or disassembly regulating polypeptide sequence, and an exogenous catalytic polypeptide. Thus, rather than inserting the exogenous polypeptide into the Cp half-dimer, it can be covalently linked to a Cp heterodimer post expression. This can be advantageous where the exogenous polypeptide may affect, for example, half-dimer expression, folding, and/or solubility if included in the half-dimer as an insertion. The exogenous polypeptide can be linked to a cysteine residue included at the half-dimer's spike tip or at its C-terminus. For example, a cysteine residue can be introduced at amino acid position 77 of HBV Cp149 via an E→C substitution. The exogenous polypeptide can also be attached to the C-terminus of a half-dimer, which will result in the attached exogenous polypeptide being located within a resulting capsid.

Similarly, dyes and fluorophores can be attached to the half-dimer. This can, for example, facilitate visualization of capsid assembly and/or in vivo translocation and binding. Dyes and fluorophores can be attached at either the half-dimer's spike tip or at its C-terminus, as provided above.

Heterodimer Multimers

The orthohepadnavirus Cp heterodimers provided herein can be engineered to aggregate into multimers. This can be accomplished by including an affinity tag, elastin-like polypeptide, or leucine zipper at the C-terminus at either a first half-dimer or a second half-dimer of a Cp heterodimer. The affinity tag, elastin-like polypeptide, or leucine zipper can be configured to aggregate several heterodimers into a desired multimer. In some embodiments, the heterodimer multimer is a hexamer (i.e., a viral capsid protein hexamer).

Figure 17:
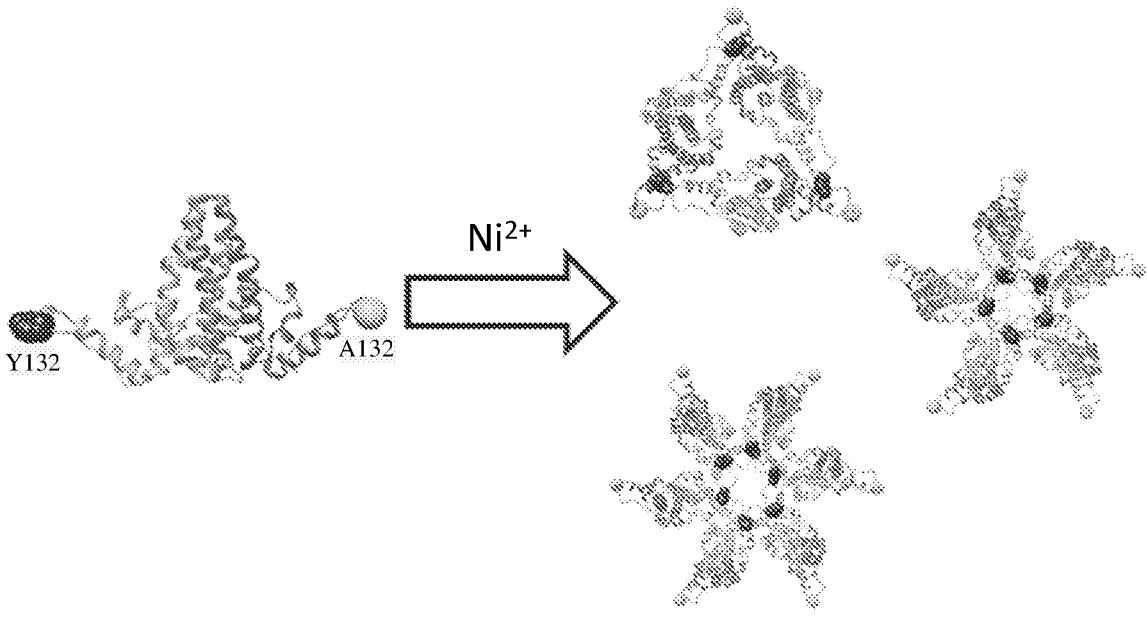
FIG. 17 depicts multimerization of a heterodimer according to certain embodiments.

In some embodiments, a polyhistidine tag (6×His (SEQ ID NO: 2)) is included at the C-terminus of a half-dimer of a Cp heterodimer. By incubating a plurality of heterodimers including polyhistidine with a divalent metal ion (e.g., $Ni^{2+}$, $Co^{2+}$, $Cu^{2+}$, or $Zn^{2+}$), the heterodimers will form multimers, including hexamers (FIG. 17). The formed multimers (e.g., hexamers) thus include multiple (e.g., 3 or more) Cp heterodimers, each including polyhistidine, and divalent metal ions.

The plurality of Cp heterodimers including polyhistidine with a divalent metal ion can be incubated in a low ionic strength buffer to promote the formation of multimers, including hexamers. The low ionic strength buffer can have an ionic strength of about 100 μM or less. The low ionic strength buffer includes a molar excess of the chelatable divalent metal (e.g., 100 μM nickel ($Ni^{++}$) for 10 μM dimer). Multimer assembly is driven by the His-tag chelation of the divalent metal ion. The low ionic strength buffer can include, for example, 50 mM HEPES, and be free of sodium chloride.

In other embodiments, an elastin-like polypeptide is included at the C-terminus of a Cp heterodimer half-dimer. Elastin-like polypeptides linked to capsid proteins have been demonstrated induce assembly of multimers and even small VLPs (van Eldijk, M. B. et al. Designing two self-assembly mechanisms into one viral capsid protein. J Am Chem Soc 134, 18506-18509 (2012)).

In other embodiments, a leucine zipper is included at the C-terminus of a Cp heterodimer half-dimer. Leucine zippers are known to be involved in the intersubunit interactions of capsid proteins of other, non-hepadnavirus viruses. By including a leucine zipper at the C-terminus of a Cp heterodimer half-dimer, this ability to link Cps together can be leveraged to cause the Cp heterodimers to form multimers.

Virus-Like Particles

Provided herein are virus-like particles (VLPs) made up at least in part by capsid protein (Cp) heterodimers described herein. VLPs are self-assembled particles made up of capsid proteins without any viral genome. VLPs can act as a nano-carrier and offer a high surface-to-volume ratio, with a large cargo capacity. VLPs show promise as a delivery system for therapeutics, and have been demonstrated to effectively target cancer cells. VLPs have also been demonstrated to be useful as vaccines. As VLPs include repetitive, high-density displays of viral surface proteins, VLPs can elicit strong T cell and B cell immune responses. VLPs cannot replicate, and offer a safer alternative to attenuated viruses. These and other uses for VLPs are known to those skilled in the art of this disclosure. Those of skill in the art will recognize the advantages provided by the Cp heterodimers described herein, which are outlined below.

VLPs can include one or more Cp heterodimers described herein. For example, VLPs can include a plurality of identical Cp heterodimers, a combination of a plurality of identical of Cp heterodimers and a plurality of identical Cp homodimers, a combination of a plurality of two or more different Cp heterodimers and a plurality of identical Cp homodimers, a combination of a plurality of identical Cp heterodimers and a plurality of two or more different Cp homodimers, or a combination of a plurality of two or more different Cp heterodimers and a plurality of two or more different Cp homodimers. The resulting VLPs can be homogenous, or can take the form of a 'mosaic'. Such mosaic VLPs, including two or more different Cp dimers (i.e., heterodimers, homodimers, or a combination thereof), can be patterned or randomly arranged.

When two or more different Cp heterodimers are included in a VLP, they can differ in: the Cp backbone forming either or both of the first half-dimer and the second half-dimer; the exogenous polypeptide inserted into the Cp heterodimer; the exogenous polypeptide linked to the Cp heterodimer; or any combination thereof. For example, a VLP can include a first population of heterodimers including a first exogenous polypeptide insertion, and a second population of heterodimers including a second exogenous polypeptide insertion, wherein the first exogenous polypeptide insertion and the second exogenous polypeptide insertion are not identical. This provides for VLPs presenting multiple different exogenous peptides on its surface. Of course, if only one type of heterodimer including an exogenous polypeptide insertion is used to form the VLPs, a single exogenous polypeptide will be present on the surface. By inserting or linking different exogenous polypeptides or other moieties to the Cp heterodimers, VLPs can be engineered to have a desired characteristic or effect, such as antigen presentation, targeted binding, fluorescence, and the like.

Any of the Cp heterodimers described herein can be incorporated into a VLP. Similarly, any of the Cp homodimers described herein can be incorporated into a VLP along with the Cp heterodimer(s). Examples of Cp homodimers that can be included in a VLP along with the Cp heterodimers described herein include: HBV Cp140; HBV Cp149; HBV Cp149-3CA; HBV Cp150; and HBV Cp183.

VLPs disclosed herein can include one or more viral capsid protein hexamers described herein.

VLPs can be loaded with one or more nucleic acid sequences, one or more polypeptides, one or more small molecules, or any combination thereof. The resulting VLP contains the one or more nucleic acid sequences, one or more polypeptides, one or more small molecules, or any combination thereof. Such VLPs can be used as a delivery system for their contents. By including appropriate exogenous polypeptides on the surface of the VLPs, such a delivery system can be specifically targeted to a cell type. For example, the VLPs can present an exogenous ligand on their surface that will bind to a cell type-specific receptor. Conversely, the VLPs can present a receptor or receptor binding site on their surface, which will bind to a cell type-specific ligand.

Methods for making VLPs are also provided. In some embodiments, the VLPs can be nucleated by the viral capsid protein hexamers described herein. Viral capsid protein hexamers can be incubated with a plurality of Cp heterodimers, a plurality of Cp homodimers, or a combination thereof. The plurality of Cp heterodimers can all be identical, or can include two or more different Cp heterodimers. The plurality of Cp homodimers can all be identical, or can include two or more different Cp homodimers.

A feature of the viral capsid protein hexamers is that following VLP formation, they can be disassembled, leaving a stable holey VLPs (i.e., holey capsids). Thus, the methods for making VLPs using viral capsid protein hexamers can also include disassembling the hexamers to form holey VLPs. Where the heterodimers that make up the viral capsid protein hexamers include a polyhistidine tag and divalent metal ions, the viral capsid protein hexamers can be disassembled using ethylenediaminetetraacetic acid (EDTA). EDTA can be used in combination with urea to ensure disassembly. As provided in the Experimental Examples, this approach can be used with HBV $Cp149_{His}Cp149_{Y132A}$ hexamers.

The holes of holey VLPs can be filled with Cp heterodimers, Cp homodimers, or a combination thereof by incubating the holey VLPs with the desired Cp heterodimers, Cp homodimers, of combination thereof. When the holey VLPs are to be loaded with one or more nucleic acid sequences, one or more polypeptides, one or more small molecules, or any combination thereof, the holes can be filled after loading.

If a plurality of Cp heterodimers are incubated with the viral capsid protein hexamers, the plurality of Cp heterodimers can include two or more populations of Cp heterodimers, wherein heterodimers of the two or more populations of Cp heterodimers are not identical. The Cp heterodimers can differ, for example, by including different polypeptide insertions or no insertion at all.

When formation of VLPs is nucleated by viral capsid protein hexamers, the resulting VLP is analogous to a Janus particle. The chemically distinct nature of the hexamer patch (or the patch created by refilling the holes of a holey VLP) relative to the remainder of the VLP results in the ability to control further modification, disassembly of the VLP, and reassembly of the VLP. Further, the hexameric patches can provide for concentrated groupings of exogenous polypeptides.

In other embodiments, a plurality of Cp heterodimer monomers can assemble into mosaic VLPs. Such VLPs are formed by incubating a plurality of Cp heterodimers described herein, or a combination of a plurality of Cp heterodimers and a plurality of Cp homodimers. The plurality of Cp heterodimers can include two or more different populations of Cp heterodimers. For example, each of the two or more different populations of Cp heterodimers can include a different exogenous polypeptide. The result is a mosaic VLP with multiple exogenous polypeptides being displayed on its surface. Similarly, the plurality of Cp homodimers can include two or more different population of Cp homodimers. Using a particular Cp homodimer or group of Cp homodimers can aid in controlling VLP assembly.

EXAMPLES

Experimental Example 1—Materials and Methods

Design of the bicistronic expression plasmid, pET11a-Cp149$_{His}$Cp149$_{Y132A}$. Two individual expression plasmids, pET11a-Cp149$_{His}$ and pET11a-Cp149$_{Y132A}$ for protein Cp149$_{His}$ and Cp149$_{Y132A}$, respectively, were synthesized. To guarantee the downstream construction for heterodimer plasmid, the expression sequences for Cp149$_{His}$ and Cp149$_{Y132A}$ were separately inserted between restriction sites for enzyme NdeI and NheI on two naked pET11a plasmids. The coding sequence for HBV Cp149 is provided by SEQ ID NO: 4, with the expression construct provided by SEQ ID NO: 6. The coding sequence for HBV Cp149$_{Y132A}$ is provided by SEQ ID NO: 5, with the expression construct provided by SEQ ID NO: 7. The following silent modifications were also made relative to the HBV adyw Cp sequence to optimize protein expression in E. coli (relative to SEQ ID NO: 4): C123A, T141C, TTCA143-146CAGC, AC161-162CT, C163A, A420G, A422G, G424A, and T438G.

Plasmid pET11a-Cp149$_{His}$ was digested with NheI and BamHI, and plasmid pET11a-Cp149$_{Y132A}$ was digested with XbaI and BamHI. Fragments carrying expression genes were recovered with the QIAquick Gel Extraction Kit. Because XbaI and NheI share the same overhang nucleosides, CTAG, both fragments were mixed and ligated together leading to the pET11a plasmid carrying a bicistronic expression gene for Cp149$_{His}$Cp149$_{Y132A}$.

Protein expression of homodimers Cp149, Cp150 and heterodimer Cp149$_{His}$Cp149$_{Y132A}$. Cp149 and Cp150 were purified from an E. coli expression system. Capsids from lysate were precipitated by ammonium sulfate, followed by size exclusion chromatography, dissociation of capsid to dimers by 3M urea, and a second round of size exclusion chromatography to isolate dimers.

For heterodimer Cp149$_{His}$Cp149$_{Y132A}$, the bicistronic expression plasmid, pET11a-Cp149$_{His}$Cp149$_{Y132A}$, was transformed into E. coli BL21(DE3) for protein expression. The purification protocol was modified based on the previously published protocol for Cp149$_{Y132A}$, Cp150, and Cp149D78S. After transformation, single colonies were inoculated in 5 mL LB media with 100 μg/mL carbenicillin at 37° C. overnight, which was then transferred into 250 mL TB media with 100 μg/mL carbenicillin for 16 hours at 37° C. without IPTG induction. 26 grams of cells were harvested out of 1.75 L TB media by centrifugation.

All following steps were finished either on ice or at 4° C., and all buffer solutions were pre-equilibrated at 4° C. Cell paste was resuspended with a similar lysis buffer except replacing 50 mM TRIS pH 7.5 by 50 mM HEPES pH 7.5 and lysed by sonication as previously published for Cp150 purification. After sonication and ammonium sulfate (AS) precipitation, the precipitated protein pellet was resuspended in 40 mL 50 mM NaHCO$_3$ pH 9, 2 mM DTT (Buffer X), then loaded onto a hand packed XK 50/100 column with Sephacryl S300 resin (GE Healthcare) and eluted overnight with Buffer X.

Heterodimer Cp149$_{His6}$Cp149$_{Y132A}$ is supposed to be an assembly incompetent dimer, with the Y132A mutation and the two monomers, Cp149$_{His6}$ and Cp149$_{Y132A}$, and should have 1 to 1 ration. To exclusively collected heterodimers, fractions were evaluated by SDS-PAGE and absorbance, and fractions meeting the two conditions were collected. Pooled fractions were further purified as Cp149$_{Y132A}$ with a HiTrap Q HP column (GE Healthcare) to remove junk proteins. Pooled fractions from the HiTrap Q step were precipitated using 20% w/v ammonium sulfate, then resuspended in 20 mL 20 mM TRIS-HCl, 50 mM NaCl, 5 mM Imidazole, 2 mM DTT (Buffer A) and loaded on a HisTrap HP column (GE Healthcare). Heterodimer Cp149$_{His6}$Cp149$_{Y132A}$ bound to the column was eluted with 43% 20 mM TRIS-HCl, 50 mM NaCl, 500 mM Imidazole, 2 mM DTT (Buffer B) after a linear gradient test. Based on SDS-PAGE evaluation, fractions with pure proteins were harvested and dialyzed into Buffer X and stored at −80° C. In all experiments, all proteins were dialyzed into 50 mM HEPES pH 7.5 prior to use. All protein concentrations were calculated using the extinction coefficient ($\epsilon_{280}$=60,900 M$^{-1}$ cm$^{-1}$) for HBV Cp149 homodimer.

SDS-PAGE and Mass spectrometry. To examine the protein purity and content, heterodimer Cp149$_{His}$Cp149$_{Y132A}$ was first diluted to 20 μM. 20 μL of Cp149 or Cp149$_{His6}$Cp149$_{Y132A}$ was mixed with 20 μL 4× protein SDS-PAGE loading buffer without β-mercaptoethanol and boiled for 8 min at 95° C. 5 μL of each reaction was loaded onto a 6%-16% SDS-PAGE for analysis. Freshly prepared Cp149$_{His6}$Cp149$_{Y132A}$ was also analyzed on a Waters Synapt G2-S mass spectrometer to determine the purity and contents.

For co-assembled capsids and holey capsids, 15 μL of each sample at 6 μM was mixed with 15 μL 4× protein SDS-PAGE loading buffer with β-mercaptoethanol and boiled for 8 min at 95° C. 15 μL of each sample was loaded onto a 6%-16% SDS-PAGE for analysis.

Size-exclusion chromatography (SEC). All the analytical experiments were carried out using a Superose 6 10/300 GL column (GE Healthcare) mounted on an HPLC system (Shimadzu) with a 0.5 mL/min flowrate. To collect fractions for further characterization, all reactions were loaded onto the same column mounted on a GE AKTApurier FPLC. For different experiments, the column was equilibrated in a corresponding buffer. For heterodimer hexamer characterization, the column was equilibrated and run with 50 mM HEPES pH 7.5. For Cp150 and hexamer co-assembly reactions, the column was run with 300 mM NaCl, 50 mM HEPES pH 7.5. For the disassembled holey capsids, the column was run with 150 mM NaCl, 50 mM HEPES pH 7.5. For the refilling reactions, the column was run with 300 mM NaCl, 50 mM HEPES pH 7.5.

Assembly of hexamer, co-assembly, disassembly, and holey capsids refilling. All concentrations mentioned are final concentrations. To assemble heterodimer hexamers, heterodimer $Cp149_{His}Cp149_{Y132A}$ was mixed with $NiCl_2$ in 50 mM HEPES pH 7.5 buffer with a 1:10 ratio of $Cp149_{His}Cp149_{Y132A}$ to $NiCl_2$ and incubated at 23° C. for 1 h. To use hexamers as nuclei for Cp150 co-assembly, a 4:1 ratio of Cp150 to $Cp149_{His}Cp149_{Y132A}$ was mixed with the pre-assembled hexamers, leading to a 4:1:10 ration of Cp150: $Cp149_{His}Cp149_{Y132A}$:$NiCl_2$ in the mixture, and incubated for 10 minutes at 23° C. Lastly, a final concentration of 300 mM NaCl, 50 mM HEPES pH 7.5 was added to the mixture and incubated at 23° C. for 24 h to assemble co-assembled capsids. Co-assembled capsids were then purified with AKTApurier FPLC.

To remove hexamers from co-assembled capsids and create holey capsids, purified capsids were mixed with 3 M urea and 100 μM EDTA and incubated at 23° C. for 24 h. Holey capsids were further purified using an Amicon Ultra-Cel with 100 kDa cutoff to removed disassembled $Cp149_{His}Cp149_{Y132A}$ subunits with 150 mM NaCl, 50 mM HEPES pH 7.5 as washing buffer and repeated 4 times. Cp150 was labeled by BODIPY-FL as published previously. 2 μM BODIPY-FL labeled Cp150, Cp150Bo, was mixed with 4 μM holey capsid first, and refilling of the holey capsids was initiated by increasing NaCl concentration to 300 mM and incubating at 23° C. for 24 h. 2 μM Cp150Bo was mixed with 300 mM NaCl as a control for the refilling reaction. To detect refilling of the holey capsids, absorbance at 280 nm for protein and 504 nm for BODIPY of each sample was collected on HPLC with 4 nm bandwidth. Fluorescence of Cp150Bo at 512 nm was collected with excitation wavelength at 504 nm using a Shimazu RF-20A detector with a 20 nm spectral bandwidth.

Charge Detection Mass Spectrometry (CDMS). CDMS allows the mass distribution to be measured for heterogeneous and high molecular weight samples that are not accessible by conventional MS. In CDMS, the masses of individual ions are determined from simultaneous measurements of each ions mass to charge ratio (m/z) and charge (z). Mass measurements are performed for thousands of ions, and then, the results are binned to yield a mass distribution. The homebuilt second-generation CDMS instrument employed here has been described previously (see Contino, N. C. & Jarrold, M. F. Charge detection mass spectrometry for single ions with a limit of detection of 30 charges. *Int. J. Mass Spect.* 345-347, 153-159 (2013)). Samples were electrosprayed using a commercial nanoelectrospray (nESI) source (Advion Triversa Nanomate®) and the resulting ions enter the instrument though a heated metal capillary. The ions pass through several stages of differential pumping to separate them from the ambient gas. They are then accelerated to a nominal energy of 130 eV/z and focussed into a dual hemispherical deflection energy analyzer (HDA) that transmits a narrow band of ion energies centred on the nominal ion energy. Ions that pass through the HDA are focussed into an electrostatic linear ion trap (ELIT) where trapped ions oscillate back and forth through a detection cylinder, in this case for 100 ms. When an ion enters the cylinder, it induces a charge which is detected by a charge sensitive preamplifier. The resulting signal is amplified, digitized, and analyzed using fast Fourier transforms. The oscillation frequency is related to the ion's m/z and the FFT magnitudes are proportional to the charge. Prior to electrospray, it is necessary to buffer exchange samples into a volatile buffer. In this case, hexamer samples were buffer exchanged into 20 mM ammonium acetate using size exclusion chromatography (Micro Bio-Spin P-6 Gel Columns, BIO-RAD).

Resistive-Pulse Sensing (RPS). Nanofluidic devices for RPS measurements were fabricated from D263 glass substrates. Each device has two V-shaped microchannels that are connected by a series of nanochannels and nanopores (FIG. 12A). Nanochannels and nanopores (FIG. 12A) were milled into the 10-μm gap between the V-shaped microchannels using an Auriga 60 focused ion beam instrument (Carl Zeiss AG). The substrate was then bonded to a D263 cover glass at 545° C. for 12 h. Reservoirs were then attached to the RPS device with epoxy.

Multicycle resistive-pulse sensing was used to measure Cp150 capsid standards, hexamer nucleated capsids, holey capsids, and refilled capsids. For these measurements, capsid samples were diluted with HEPES buffered 1M NaCl to suitable concentrations (~0.1 μM dimer). For ping-pong experiments, a device with 4-pores in series was used. A potential was applied across the nanochannel and current was monitored using an Axopatch 200B (Molecular Devices, LLC) connected through a data acquisition card (PCIe-6353, National Instruments). Changes in current were analyzed, in real time, with a LabVIEW program (National Instruments) with an embedded MATLAB script (Math-Works). A threshold for pulses was determined by comparison to the baseline current. To accomplish a ping-pong experiment, after a pulse was detected for each of the four nanopores, the potential was reversed. For each particle used in the reported size distributions, at least 84 pulses were recorded, equivalent to 10.5 cycles back and forth through the RPS device. The two most abundant populations shown in the size distributions corresponded to T=3 capsids and T=4 capsids, and their peak positions were aligned to their corresponding numbers of dimers (90-mer and 120-mer). For easier visualization of populations relative to each other, the histograms of the capsids in each sample were normalized to the same total number of counts.

Negative stain electron microscopy (EM) and data processing. $Cp149_{His}Cp149_{Y132A}$ hexamers were purified using AKTApurier FPLC, and 4 μL of such sample was applied to a glow-discharged carbon film with a 300-mesh Cu grid immediately and stained with 0.75% uranyl formate. During the grid preparation, the grid was washed twice using ddH$_2$O, blotted using filter paper and air dried. Images were collected on a JEOL JEM 1400Plus transmission microscope equipped with a Gatan Oneview 4k×4k COMS camera at a nominal magnification of ×50,000 using the low-dose conditions. A total of 165 micrographs were collected and 55261 particles were semi-auto-boxed using e2boxer_old.py from EMAN2 and subjected to two rounds of reference-free two-dimensional (2D) classification using RELION (version 2.1). Selected 900 particles from 6 classes with clear definition for hexamers were used to build an initial model with C1 symmetry. Overall, 5,755 particles were selected for hexamer 3D auto-refinement with C6 symmetry, resulting in a 17 Å hexamer density map (Table 3).

TABLE 3

Statistics for negative stain EM data collection and processing.

| Dataset | Hexamer |
|---|---|
| Data collection | |
| Microscope | JEOL JEM 1400Plus |
| Nominal magnification | 50,000 |
| Voltage (kV) | 120 |
| Electron exposure $(e^-/Å^2)$ | 20 |
| Defocus range (μm) | −1.0 to −4.0 |
| Pixel size (Å) | 2.3 (Binned 4.6) |
| Reconstruction (RELION) | |
| Symmetry imposed | C6 |
| Micrograph number | 165 |
| Initial particle number | 55261 |
| Final particle number | 5755 |
| Map resolution (Å) | 17 |
| FSC threshold | 0.143 |
| EMDB accession code | EMD-22133 [https://www.emdataresource.org/EMD-22133] |

Cryo-EM and holey capsid reconstruction. Samples of holey capsids were purified through the AKTApurier FPLC and concentrated to 20 μM using an Amicon Ultra-Cel with 100 kDa cutoff. Grids preparation, data collection and image processing followed previously published protocol (Schlicksup, C. J. et al. Hepatitis B virus core protein allosteric modulators can distort and disrupt intact capsids. *Elife* 7, doi:10.7554/eLife.31473 (2018)). Simply, 4 μL of the concentrated holey capsids was applied to a glow-discharged UltraAuFoil R2/2 holey gold film grid and repeated 4 times to enrich particles on the grid, and then vitrified using a ThermoFisher Vitrobot (Mark IV, blot time: 15 s, blot force: 0, wait time: 25 s). Grids were imaged using a Thermo Scientific Talos Artica microscope operated at 200 kV. Low-dose (~30 e-1/$Å^2$) cryo-EM images, at a nominal magnification of 120,000×(1.128 Å per pixel), were collected on a Falcon III direct electron detecting camera in electron counting mode with defocus range from −1 to −3 μm. A total of 1,366 movie frames were collected using the EPU automated data collection software. Contrast transfer function parameters were estimated using ctffind4.

A total of 13,904 particles were manually boxed out of 300 micrographs using the e2boxer_old.py from EMAN2 and subjected to reference-free two-dimensional (2D) classification using RELION (version 2.1). 2D classes with clear density were selected as reference templates for particle auto-picking from all micrographs using Auto-Picking software in RELION. A total of 65,728 particles were auto picked and subjected to reference free 2D classification in RELION. After discarding classes with blurred density and deformed structures, 41,057 particles in 21 classes were left for further reconstruction. The same 21 classes were used to build an initial model de novo using C1 symmetry in RELION. To capture all possible capsid conformations, C1 symmetry was applied through all 3D refinement process. The initial model was used as template for 3D classification to separate class of complete capsids and class of holey capsids. 23,478 particles from the closed shell capsid class was auto-refined to reconstruct a complete capsid model. The remaining 17,579 particles were further divided into two classes, 9,697 particles for class with a small hole and 7,882 particles for another class with a big hole, in a 3D classification process. All three classes were refined independently using their own models from the 3D classification results, a complete capsid, a holey capsid with a small hole, and a holey capsid with a big hole. Only the complete capsid model had enough particles to reach a sub-nanometer resolution for B-factor sharpening in post-processing step. Lastly, the complete capsid was refined to 6.2 Å with a calculated B-factor of −203 $Å^2$, the holey capsid with small hole was refined to 10.8 Å and the holey capsid with a big hole was refined to 12.9 Å (Table 4).

TABLE 4

Statistics for cryo-EM data collection and processing.

| Dataset | Holey capsid mixture | | |
|---|---|---|---|
| Data collection | | | |
| Microscope | Thermo Scientific Talos Artica | | |
| Nominal magnification | 120,000 | | |
| Voltage (kV) | 200 | | |
| Electron exposure $(e^-/Å^2)$ | 30 | | |
| Defocus range (μm) | −0.6 to −4.0 | | |
| Pixel size (Å) | 1.128 (Binned 4.512) | | |
| Reconstruction (RELION) | | | |
| Symmetry imposed | C1 | | |
| Micrograph number | 1366 | | |
| Initial particle number | 65728 | | |
| Capsid type | Complete capsid | Hexamer holey capsid | Double hexamer holey capsid |
| Final particle number | 23478 | 9697 | 7882 |
| Map resolution (Å) | 6.2 | 10.8 | 12.9 |
| FSC threshold | 0.143 | 0.143 | 0.143 |
| EMDB accession code | EMD-22132 | EMD-22134 | EMD-22135 |

Figure 2A:
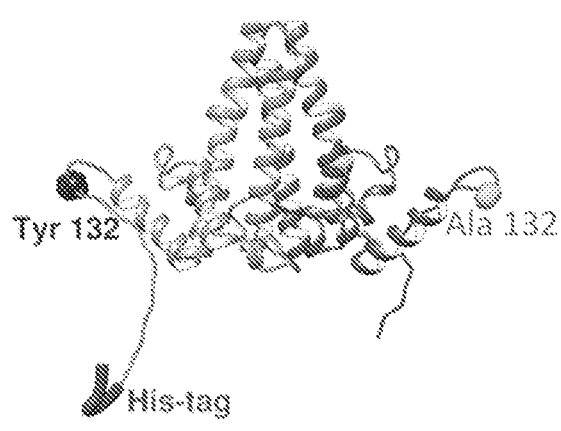
FIG. 2A depicts a model of a modified heterodimer according to certain embodiments.
Figure 2B:
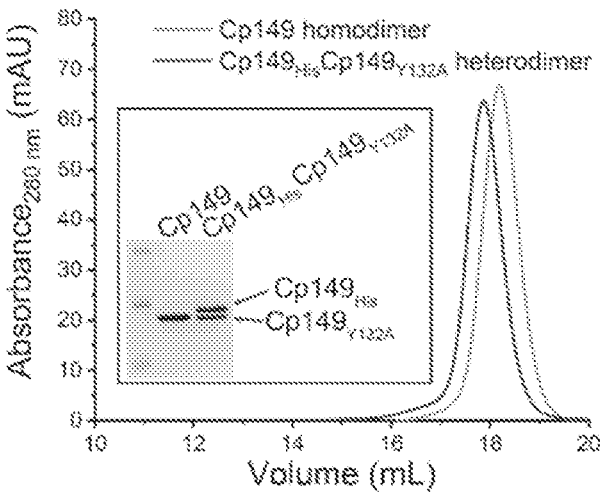
FIG. 2B depicts size-exclusion chromatography results and a photograph of an SDS-PAGE gel demonstrating successful purification of a heterodimer according to certain embodiments.
Figure 2C:
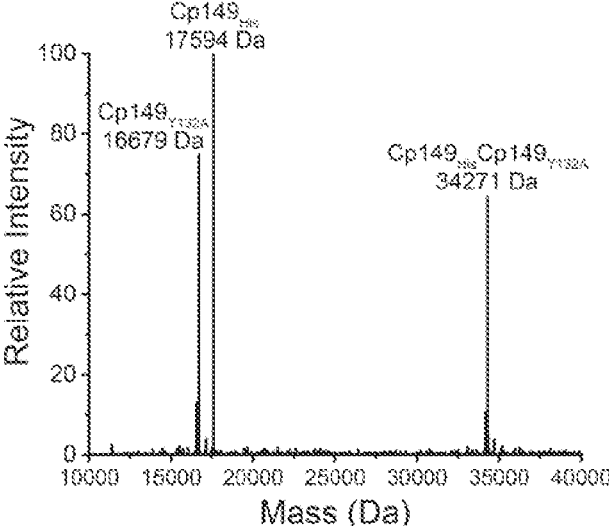
FIG. 2C depicts native mass spectrometry results obtained with a heterodimer according to certain embodiments.
Figure 6:
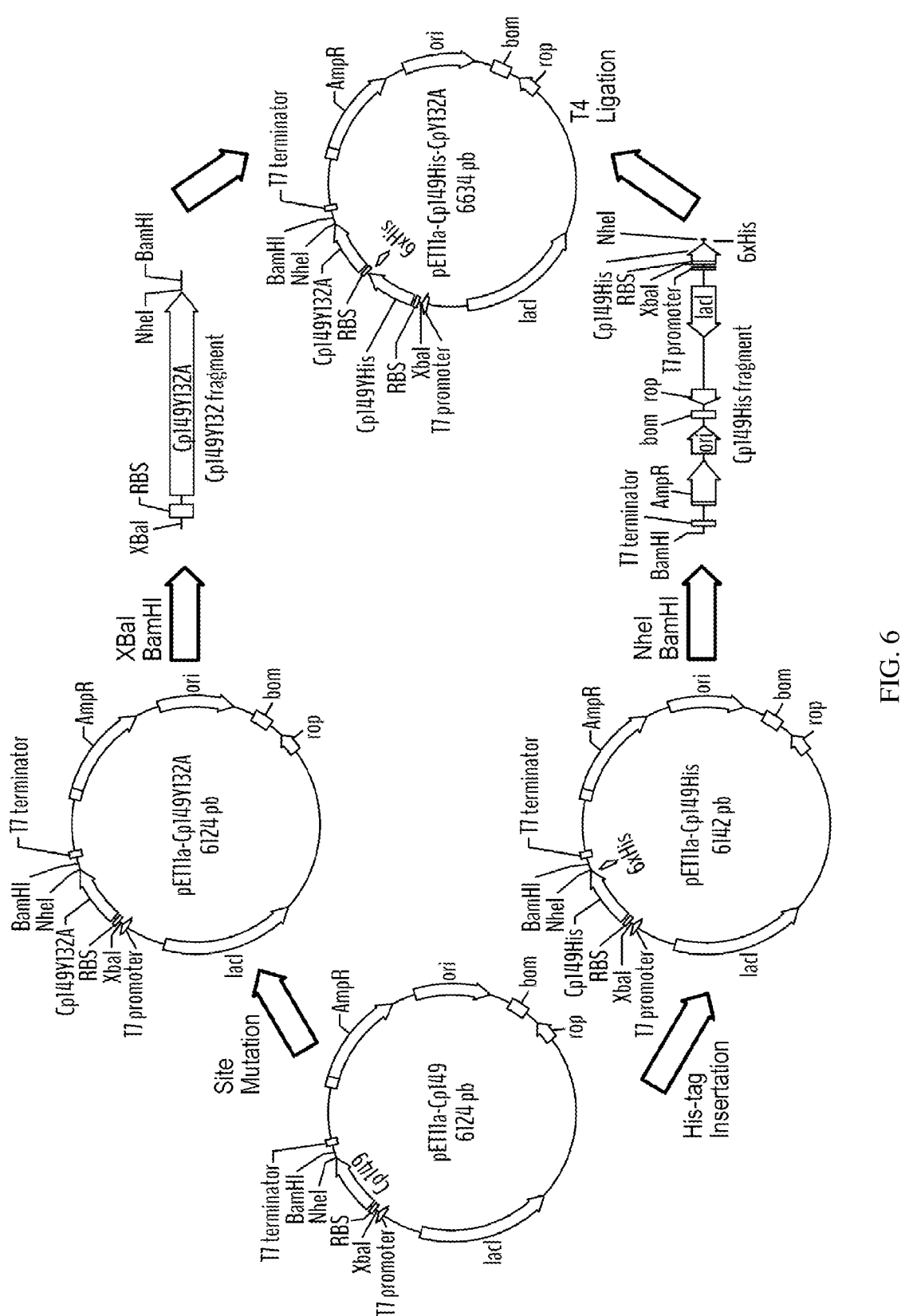
FIG. 6 is a schematic depicting the design of a bicistronic plasmid for heterodimer expression according to certain embodiments. Figure discloses "6×His" as SEQ ID NO: 2.

Experimental Example 2—Purification and Characterization of Heterodimer $Cp149_{His}Cp149_{Y132A}$ A bicistronic expression plasmid (FIG. 6) was designed to express an asymmetric heterodimer—$Cp149_{His}Cp149_{Y132A}$. This approach, referred to as the 'splitcore' approach, has been used to split a single monomer into two segments, which can still dimerize, to incorporate oversized proteins for vaccine development (Walker, A., Skamel, C. & Nassal, M. SplitCore: an exceptionally versatile viral nanoparticle for native whole protein display regardless of 3D structure. Sci Rep 1, 5, doi:10.1038/srep00005 (2011)). The bicistronic plasmid carries a single promoter followed by a gene for each monomer, $Cp149_{His}$ and $Cp149_{Y132A}$. Each gene has its own ribosome binding site (RBS). Following *E. coli* expression, $Cp149HisCp149_{Y132A}$ was purified as a dimer and characterized. Purification included size exclusion chromatography to remove any assembly-competent $Cp149_{His}$ homodimer and Ni chromatography to isolate His-tagged heterodimer from $Cp149_{Y132A}$ homodimer. The yield of purified protein was ~50 mg per liter of LB broth. $Cp149_{His}Cp149_{Y132A}$ eluted as a single peak on size-exclusion chromatography (SEC) at the same position as homodimer Cp149 (FIG. 2B). $Cp149_{His}Cp149_{Y132A}$ was resolved on SDS-PAGE, showing approximately equal amounts of two bands corresponding to the Y132A and the His-tag monomers (FIG. 2B, inset). Native mass spectrometry (MS) of heterodimer $Cp149_{His}Cp149_{Y132A}$ showed three peaks corresponding to $Cp149_{His}$ monomer, $Cp149_{Y132A}$ monomer, and heterodimer comprised of $Cp149_{His}$ and $Cp149_{Y132A}$ (FIG. 2C). There was no evidence of either $Cp149_{His}$ or $Cp149_{Y132A}$ homodimers in the MS analysis.

Efficient expression of highly purified heterodimer was an important step towards asymmetric assembly in this study. An asymmetric dimer can also be useful for vaccine development and other applications. The splitcore system allowed incorporation of large inserts but still generated a symmetric dimer. An HBV tandem dimer comprised of two monomers linked by a short peptide was developed (Peyret, H. et al. Tandem fusion of hepatitis B core antigen allows assembly of virus-like particles in bacteria and plants with enhanced capacity to accommodate foreign proteins. *PLoS One* 10, e0120751 (2015); Holmes, K. et al. Assembly Pathway of Hepatitis B Core Virus-like Particles from Genetically Fused Dimers. *J. Biol Chem* 290, 16238-16245, (2015)). However, the tandem dimer had low yield and generated many aggregates when reproduced by the inventors, indicating that the linkage between monomers may have led to misfolding. The bicistronic heterodimer expression system retained monomer integrity, while still providing the opportunity to modify each monomer independently.

Figure 7:
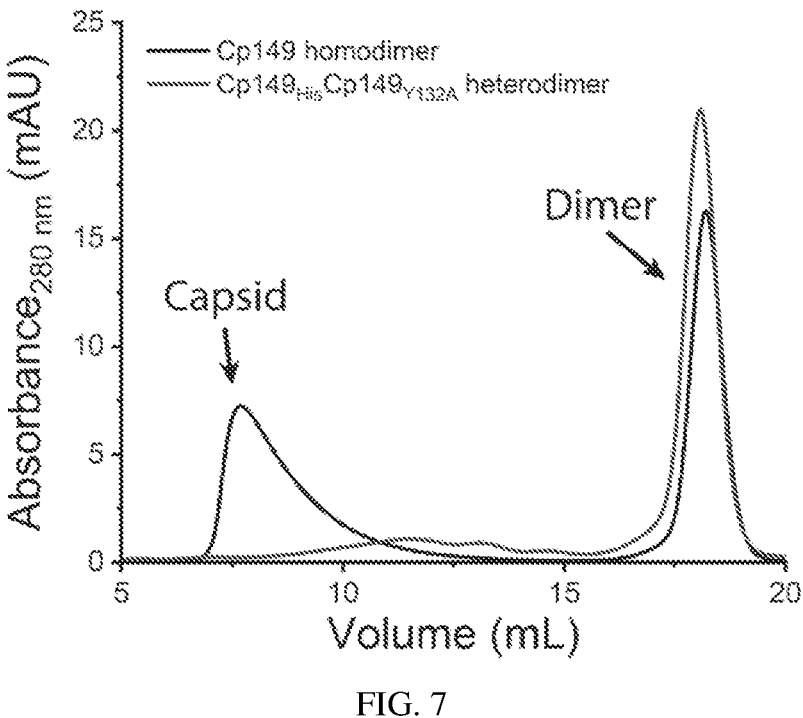
FIG. 7 depicts size-exclusion chromatography results demonstrating assembly of Cp149 homodimer and $Cp149_{His}Cp149_{Y132A}$ heterodimer.

Experimental Example 3—Heterodimer $Cp149_{His}CP149_{Y132A}$ Assembles as a Hexamer Because the generated heterodimer carries the assembly-incompetent mutation Y132A, the inventors compared the assembly induced by high ionic strength (300 mM NaCl) of $Cp149_{His}Cp149_{Y132A}$ and wild-type homodimer Cp149. $Cp149_{His}Cp149_{Y132A}$ failed to assemble capsids, and no stable intermediates were isolated under conditions where Cp149 assembled readily (FIG. 7).

Figure 3A:
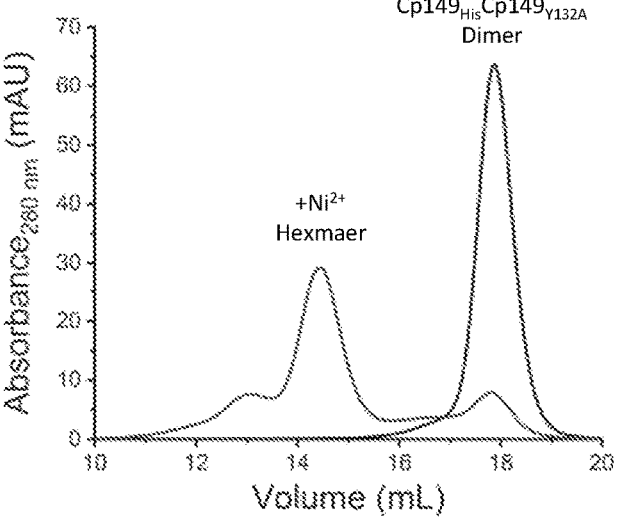
FIG. 3A depicts size-exclusion chromatography results demonstrating hexamer formation with heterodimer in response to $Ni^{2+}$ according to certain embodiments.
Figure 3C:
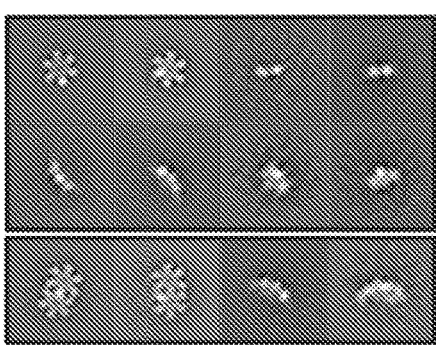
FIG. 3C is a negative-stain electron micrograph depicting heterodimer multimers.
Figure 3B:
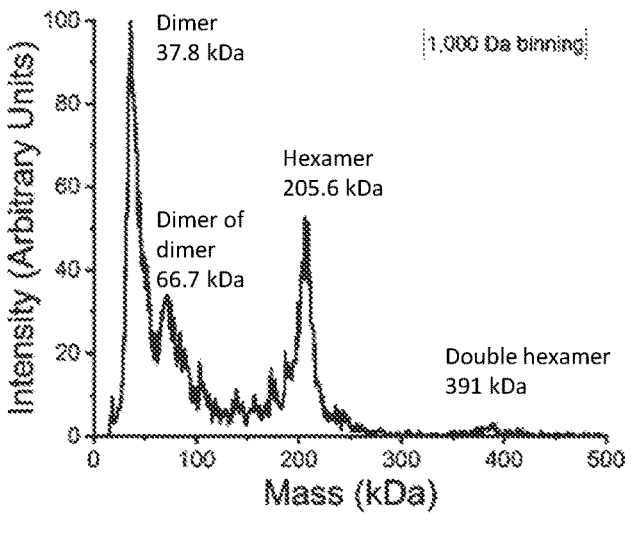
FIG. 3B depicts results from charge detection mass spectrometry demonstrating major species formed during heterodimer aggregation experiments.
Figure 3D:
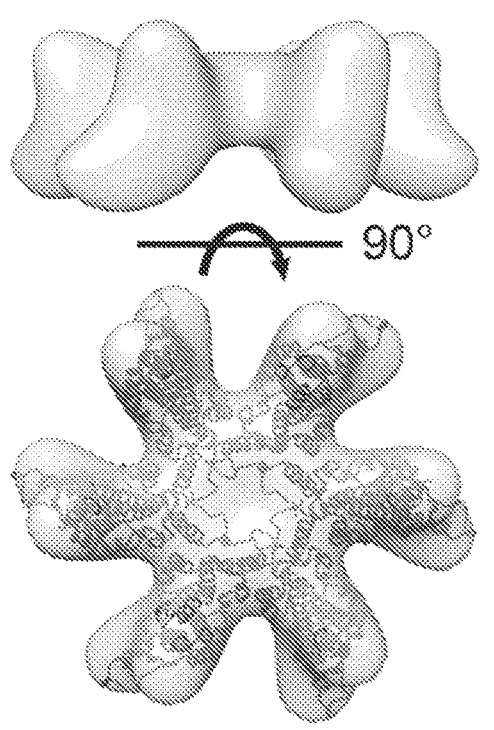
FIG. 3D is a 3D density map illustrating the heterodimer hexamer complex.
Figure 8:
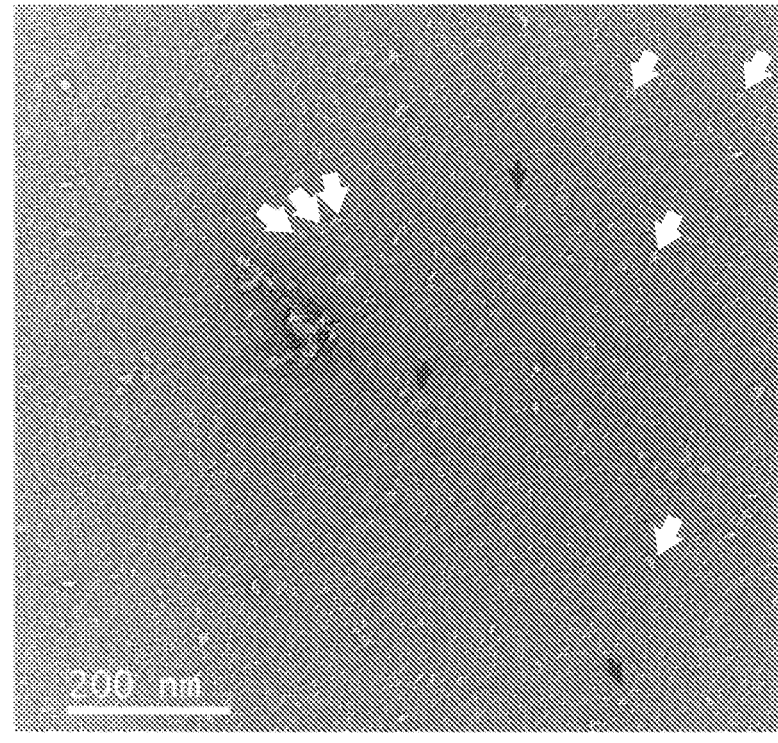
FIG. 8 is a negative stain micrograph showing hexamers (white arrows) and double hexamers (black arrows).

The inventors then tested assembly of $Cp149_{His}Cp149_{Y132A}$ in response to $Ni^{2+}$ at low ionic strength, taking advantage of the His-tag without involving ionic strength-driven assembly (FIG. 3). 10 μM heterodimer and 100 μM $NiCl_2$ was typically used for these reactions. As observed by SEC, $Cp149_{His}Cp149_{Y132A}$ assembled into heterogeneous complexes that are larger than dimers. Using charge detection mass spectrometry (CDMS), a single molecule native mass spectrometry technique capable of resolving the masses of complex mixtures, it was found that major species were free dimers, dimers of dimers, and hexamers, with some putative 11-dimer double hexamers (calculated masses 34.3, 68.6, 205.6, 377.0 kDa, respectively, with retention of water and salts contributing to offset of peaks) (FIG. 3B). The larger complexes were isolated by SEC and their presence confirmed by negative-stain electron microscopy (EM) (FIG. 8). Particles from micrographs were semi-manually selected and subjected to 2D classification, resulting in top and side views of hexamers and double hexamers (FIG. 3C). Due to the limited number of particles, a density map of double hexamer was not reconstructed. The top 8 classes were selected for reconstructing a 3D density map that reached 17 Å resolution. The resulting density map confirmed assembly of capsid-like hexamers by $Cp149_{His}Cp149_{Y132A}$ (FIG. 3D). A hexamer molecular model, isolated from an HBV capsid, fit well into the density. Thus, unlike symmetric homodimers, which assemble into capsids with very low concentrations of intermediates, asymmetric $Cp149_{His}Cp149_{Y132A}$ heterodimers assemble to hexamers or double hexamers and then assembly stops.

Experimental Example 4—$Cp149_{His}Cp149_{Y132A}$ Hexamers Co-Assemble with Homodimers While the Y132A mutant is assembly incompetent on its own, it can co-assemble with Cp149. The inventors reasoned that the hexameric complex that assembled in response to $Ni^{2+}$ could nucleate further assembly, because each incoming dimer will make two contacts to the nucleating hexamer, only one of which was compromised by the Y132A mutation. Thus, the Y132A may weaken the initial steps of assembly but will not prevent it. To test this hypothesis, preformed hexamers were co-assembled with homodimers, in effect making a Janus particle with a nucleus patch and a much larger homodimer patch. Cp150 homodimers were chosen because the resulting capsids can crosslink through C150 disulfide formation, yielding capsids that are stable even in 5 M urea. In the co-assembly reaction, the homodimer component would be sturdy enough to allow subsequent removal of the heterodimer hexamers.

Figures 4A, 4B, 4C:
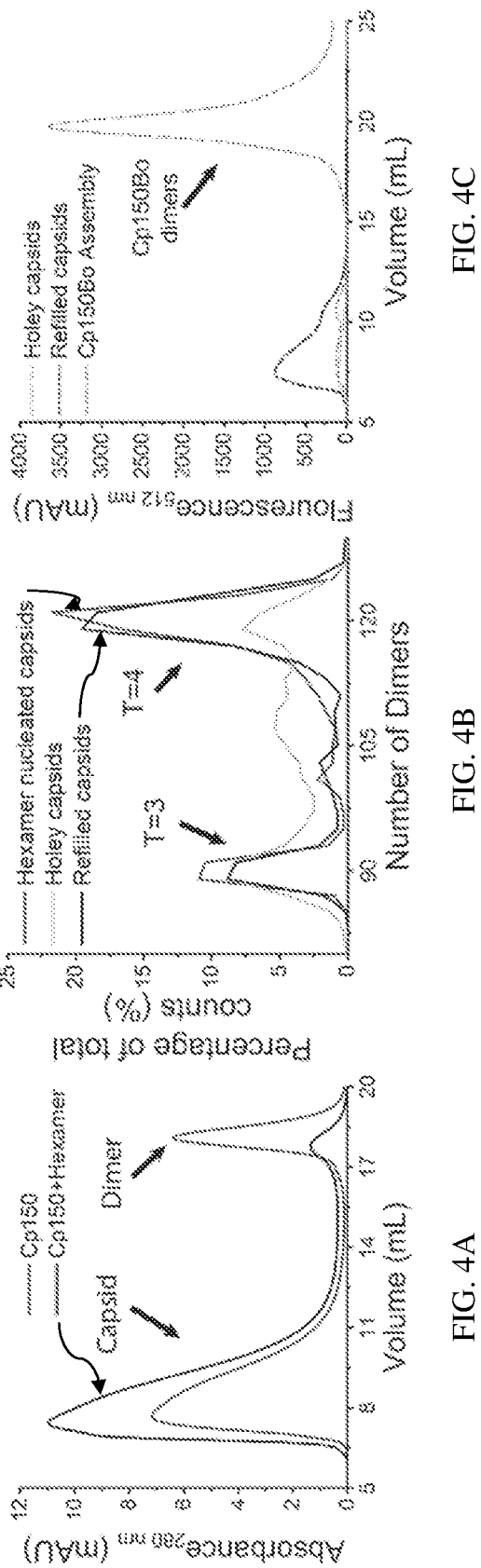
FIG. 4A depicts size-exclusion chromatography results following heterodimer hexamer incubation with homodimers.
FIG. 4B depicts resistive pulse sensing analysis results from co-assembled capsids (heterodimer hexamers+homodimer), holey capsids, and surface-refilled capsids.
FIG. 4C depicts size-exclusion chromatography results using a fluorescence detector demonstrating co-eluting of a fluorescent homodimer with surface refilled capsids.
Figure 9:
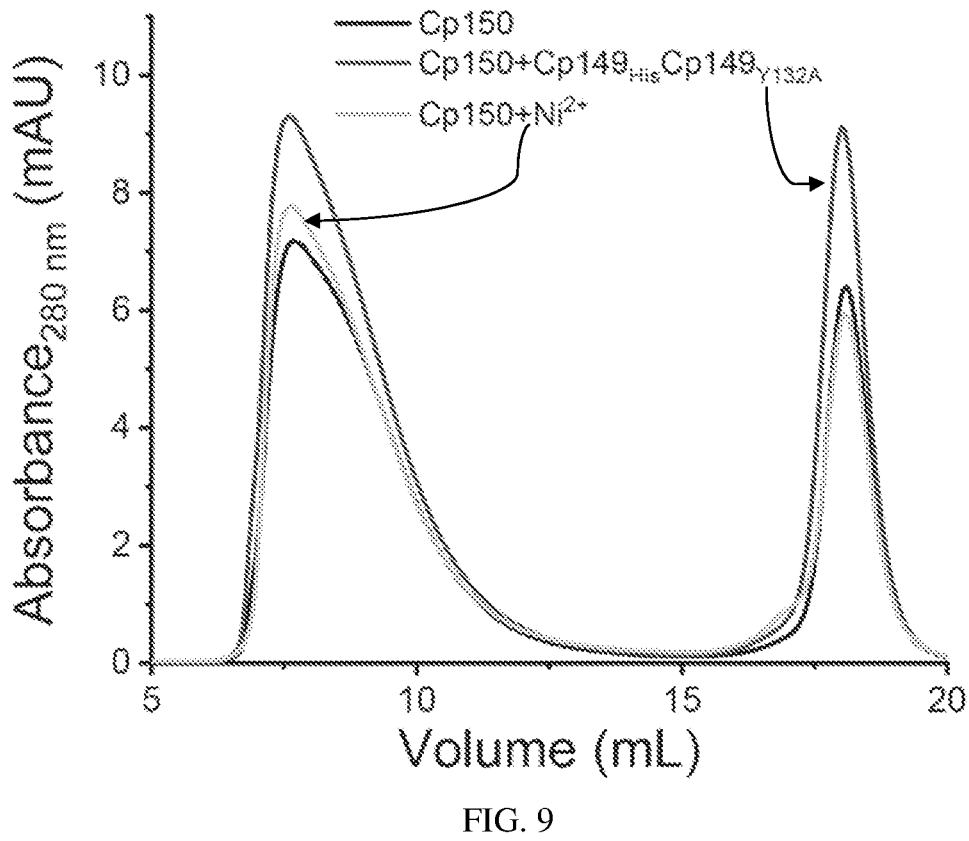
FIG. 9 depicts size-exclusion chromatography results demonstrating co-assembly of Cp150 homodimer and $Cp149_{His}Cp149_{Y132A}$ heterodimer.
Figure 10:
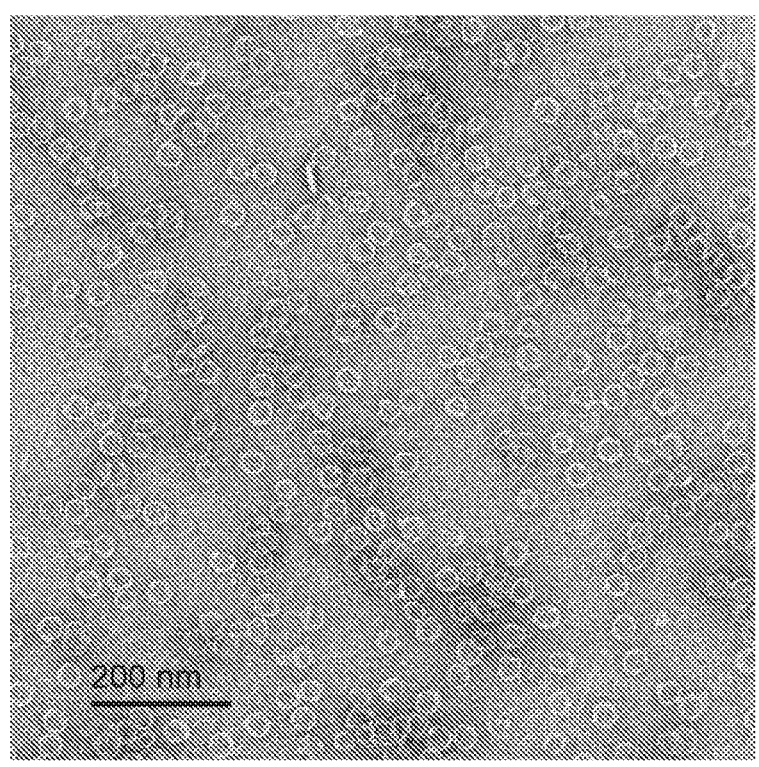
FIG. 10 is a negative stain micrograph showing $Cp149_{His}Cp149_{Y132A}$ heterodimer and Cp150 dimer co-assembled capsids.

The inventors observed that although heterodimer polymerization stops at hexamers, hexamers can nucleate ionic strength-driven (300 mM NaCl) assembly of Cp150 homodimers, forming hybrid capsids; adding heterodimer hexamers to an assembly reaction promoted assembly and decreased the apparent pseudo-critical concentration of assembly (FIG. 4A). As a control, $Ni^{2+}$ at a concentration of 100 μM had no measurable effect on Cp150 assembly (FIG. 9). Free $Cp149_{His}Cp149_{Y132A}$ heterodimers can co-assemble with Cp150 to form morphologically normal capsids, but there was no evidence that the different classes of subunit segregate (FIGS. 9 and 10).

Structural and model studies have suggested that a trimer of dimers acts as the nucleus in normal HBV capsid assembly. Here, the inventors showed that artificially created hexamers can also function as nuclei to promote assembly. It indicates that capsid assembly can progress by various pathways that might arise from different types of nuclei.

Experimental Example 5—Resection of Hybrid Capsids to Holey Capsids

Figure 11A:
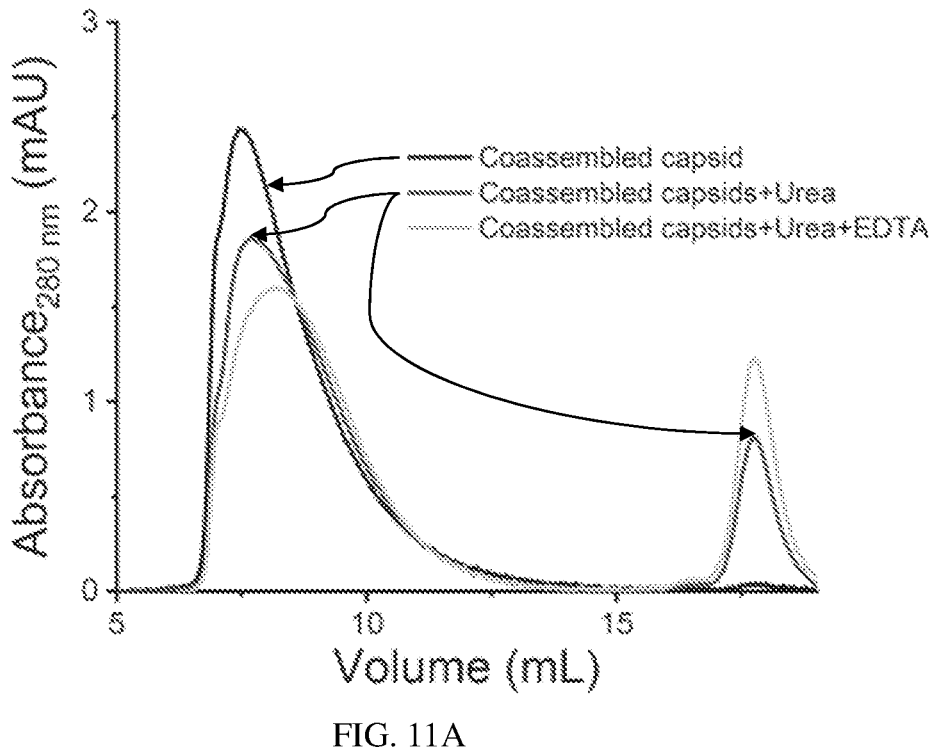
FIG. 11A depicts size-exclusion chromatography results demonstrating that urea and EDTA treatment of co-assembled capsids releases more dimers than urea treatment alone.
Figure 11B:
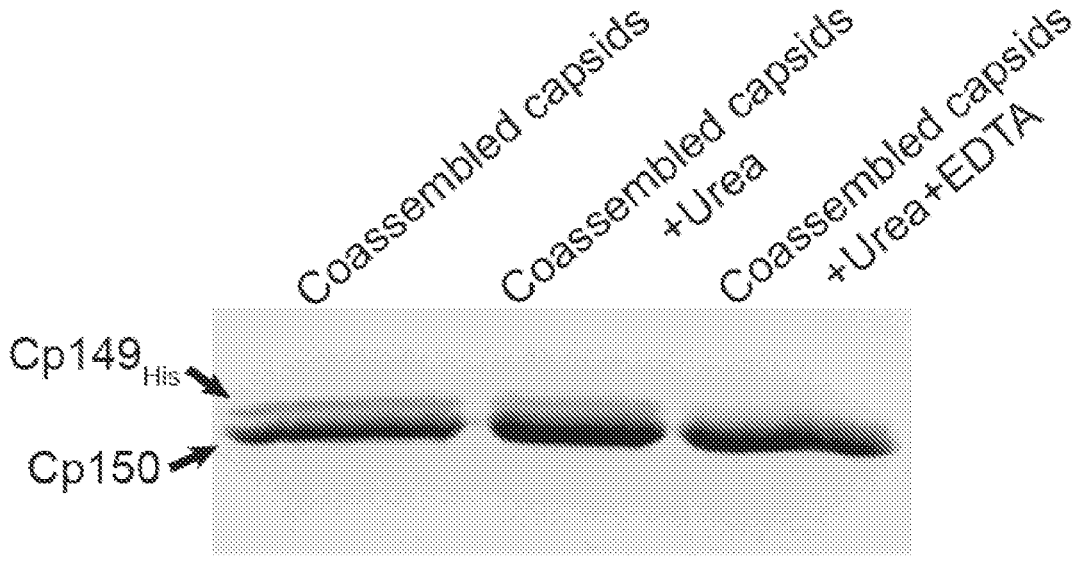
FIG. 11B is a photograph of an SDS-PAGE gel demonstrating that urea and EDTA treatment significantly reduces the amount of $Cp_{His}$ monomer in holey capsids, indicating loss of heterodimer hexamers from co-assembled capsids.

Previously, the inventors attempted to generate holey capsids by removing modified subunits that had been incorporated stochastically; they were unable to identify regular, contiguous patches by this method (Lee, L. S. et al. A Molecular Breadboard: Removal and Replacement of Subunits in a Hepatitis B Virus Capsid. Protein Sci. 26(11): 2170-2180. Epub 2017 Sep. 16. (2017)). However, the instant Janus capsids have a heterodimer hexamer patch in a body of crosslinked Cp150. The inventors hypothesized that removing the heterodimer hexamers will leave Cp150 holey capsids intact due to their exceptional stability. To test this hypothesis, the inventors purified hybrid capsids from a co-assembly reaction and removed heterodimer hexamers with a cocktail of 100 μM EDTA and 3 M urea. EDTA will disrupt the $Ni^{2+}$ mediated interaction between His-Tags. Urea at 3 M weakens Cp-Cp interactions without unfolding dimer structures, allowing the heterodimer $Cp149_{His}Cp149_{Y132A}$ dimers to dissociate from the hybrid capsids. EDTA and urea treatment decreased the amount of $Cp149_{His}$ associated with the presumably holey capsids based on SDS-PAGE and led to altered elution of capsid-sized particles on SEC (FIG. 11).

Figures 13A, 13B, 13C:
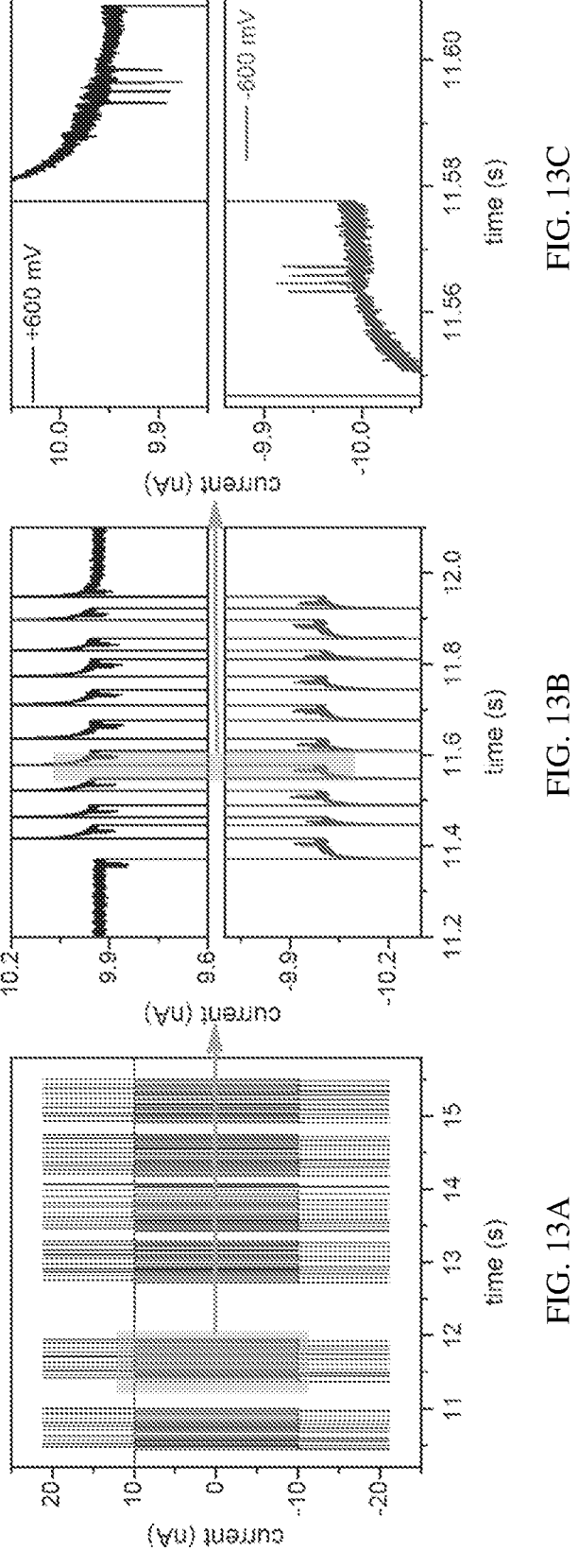
FIG. 13A depicts current traces from multicycle resistive-pulse sensing from six Cp150 capsids.
FIG. 13B depicts current traces from multicycle resistive-pulse sensing from a single capsid cycled back and forth 10.5 times.
FIG. 13C depicts current traces from multicycle resistive-pulse sensing from a capsid traveling through the four nanopores of the devices depicted in FIG. 12A.

To validate the presence of holey capsids and not the selective dissociation of hexamer-enriched capsids, the inventors analyzed purified holey capsids by resistive pulsive sensing (RPS). In RPS, solute displaces a proportional amount of electrolyte from a nanopore, resulting in a deflection of the current that is proportional to the volume of a single particle (FIGS. 12 and 13). It is a particularly powerful approach for working with low protein concentrations in the presence of non-volatile solutes. Using Cp150 assembly as standard (FIG. 14), the inventors found that EDTA and urea reduced the proportion of 120-dimer T=4 capsids, had little effect on the proportion of 90-dimer T=3 particles, and introduced a heterogeneous mixture of incomplete, stable capsids (FIG. 4B). The remaining T=4 and T=3 capsids may be assembled exclusively from Cp150 homodimers. This result confirmed that co-assembled $Cp149_{HisC}p149_{Y132A}$ hexamers can be removed from T=4 particles, leaving asymmetric holey capsids (it may be that T=3 particles are not nucleated by hexamers). Given that a 120-dimer capsid losing a single hexamer should have 114 dimers remaining, many capsids apparently had more than a hexamer or double hexamer of heterodimers removed.

Experimental Example 6—Cryo-EM Reconstruction of Holey Capsids

To unambiguously confirm that asymmetric holey capsids had been created, the inventors characterized the species in a resection reaction with cryo-EM. As predicted from the RPS results, raw micrographs of holey capsids showed a mixture of compete capsids and capsids with open edges (FIG. 5A). 41,057 particles were selected and processed for 3D image reconstruction. Through the whole reconstruction process, C1 symmetry was applied to avoid losing unique features that would have been overwritten if icosahedral symmetry averaging had been used.

Figures 5A, 5B, 5C, 5D, 5E, 5F:
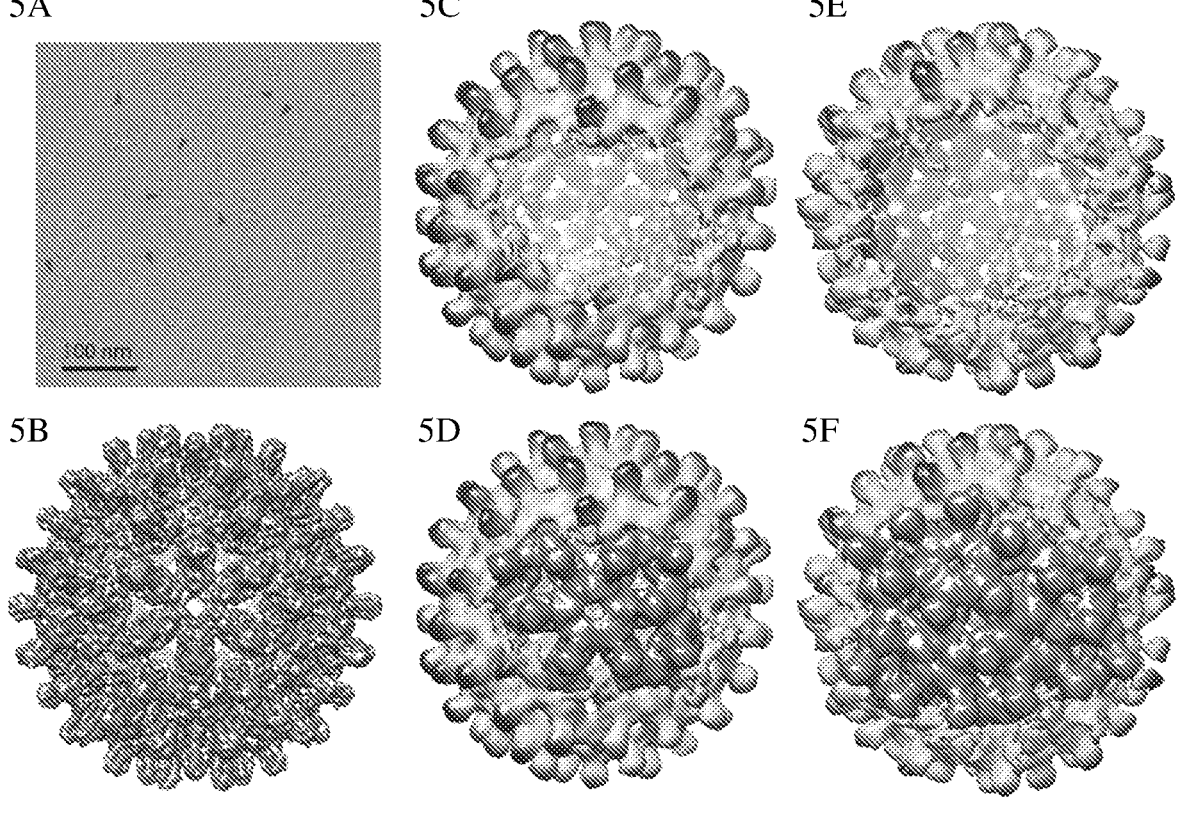
FIG. 5A is a cryo-electron micrograph depicting a holy capsid sample, with several obvious holey capsids indicated by an arrow.
FIGS. 5B-5F depict 10.8 Å resolution density maps for a holey capsid according to certain embodiments.

After 2D classification, the dataset was divided into two sets, one for complete capsids (23,478 particles) and the other for asymmetric holey capsids (17,579 particles). The dataset for complete capsids yielded a 6.2 Å resolution density map showing an apparently symmetrical 120-dimer capsid, though only C1 symmetry was applied (FIG. 5B). Some capsids included in the complete capsid dataset may have had holes that were obscured by particle orientation. The holey capsid dataset was further divided into two sets by 3D classification, based on the size of the hole. In the end, 9,697 particles were used to reconstruct a 10.8 Å resolution density map for a holey capsid missing around a hexamer of dimers (FIG. 5C). The remaining 7,882 particles were reconstructed to yield a 12.9 Å resolution density map for a holey capsid missing approximately two hexamers (FIG. 5E). The two holey capsid density maps never reached the same resolution as the 120-dimer capsid density map. This was likely due to the use of fewer particles, particle heterogeneity, and potentially the greater flexibility of holey capsids.

To quantify the number of missing dimers on both reconstructions, the inventors overlaid density maps for holey capsids at 1.3σ contour level on the density map for the 120-dimer capsid density map. For the capsid with the smaller hole, density was missing for ~9 dimers centered around a hexamer (FIG. 5D). For the capsid with the bigger hole, ~18 dimers were missing from a hole that could be filled by a double hexamer and a pentamer (FIG. 5F). Based on RPS, there was no clear peak for holey capsids that lost exactly a hexamer or a double hexamer during capsid resection. Careful examination of both holey density maps showed degraded density close to edge of the hole, suggesting that particles used for reconstruction were not homogeneous. This heterogeneity likely arose for one or more reasons: i) additional heterodimers could have associated with the built-in hexamer or the double hexamer during the co-assembly reaction, which would result in heterogeneity at edge of the hole, and ii) although the majority of the Cp150 homodimers crosslinked, dimers on the edge of the hole may not have crosslinked and were thus labile when exposed by resection. The heterogeneity of the holes observed by cryo-EM matches well with the apparent heterogeneity defined by RPS of holey capsids (FIG. 4B).

Experimental Example 7—The Surface of Holey Capsids Can be Refilled to Create Asymmetric, Un-Holey Capsids Early attempts to characterize assembly pathways showed intermediates with sizes similar to holey capsid species that could proceed to assemble. However, the inventors were unable to structurally characterize and isolate them, which may be due to their rarity and instability. The inventors reasoned that the holey capsids can also proceed to assemble to 120-dimer un-holey capsids, making them useful for containing cargo and for displaying surface features that were not part of the original nucleus or the capsid body. In effect, holey capsids are models of on-path assembly intermediates.

To test the ability to refill the surface of the holey capsids, the inventors introduced a fluorescent homodimer, Cp150Bo, which has a BODIPY fluorophore attached to residue cysteine 150 of Cp150. After the reassembly reaction, using RPS, the amount of heterogenous holey capsids decreased nearly to the baseline and the amount of 120-dimer capsids, indistinguishable from control T=4 capsids, increased (FIG. 4B). This result indicated that holey capsids are assembly-active polymers to which Cp150Bo homodimers can be added. The appearance of absorbance at 504 nm (FIG. 15B) and bright fluorescence at 512 nm for BODIPY fluorophore in chromatographic separations of un-holey capsids confirmed the addition of Cp150Bo (FIG. 4C). As a control, capsids of pure Cp150Bo are dimly fluorescent (FIG. 4C) because BODIPY fluorophores are close to each other in the capsid interior, leading to fluorescence quenching. In surface-refilled holey capsids, there were no adjacent BIDIPY fluorophores on the edges of holes, leaving fluorophores unquenched. The inventors were able to quantify the amount of Cp150Bo eluting with capsid by comparing the absorbance for BODIPY per capsid between the surface-refilled holey capsids and Cp150Bo capsid (FIG. 15). The Abs504/Abs280 ratio of both samples was calculated, and it was estimated that ~16 Cp150Bo dimers were added to one holey capsid. The number of dimers in the refilled surface aligned well with the RPS and Cryo-EM estimation.

For the holey capsid sample, the inventors did not observe BODIPY absorbance at 504 nm or fluorescence (FIGS. 4C and 15). For the Cp150Bo assembly control, the inventors observed absorbance at 280 nm and 504 nm for both capsids and dimers. The assembled capsids and the unassembled dimers roughly had the same peak areas in both absorbance chromatographs, indicating they have the same amount of protein. However, little BODIPY fluorescence was observed for capsids compared to the strong fluorescence of unassembled dimers (FIG. 4C), which is consistent with the fluorescence quenching previously reported for these capsids. However, for the refilled holey capsid sample substantial fluorescence resulting from unquenched fluorophores was observed. No free dimer was observed, indicating they had assembled or were bound into relative high affinity sites.

TABLE 5

| | Cp150Bo at 7.5 mL (mAU) | Refilled capsid at 7.5 mL (mAU) |
|---|---|---|
| Abs280 | 1.1 | 7.4 |
| Abs504 | 1.9 | 1.7 |
| Abs280/Abs504 for Cp150Bo | 0.579 | Not relevant |
| A280 attributed to Cp150Bo | 1.1 | 0.98 |

These absorbance data allowed the inventors to quantify the amount of Cp150Bo in the capsid peak. The data were collected on an HPLC equipped with a diode array detector and a fluorescence detector, so that the whole spectrum is measured at one time. Using the A280/A504 for the Cp150Bo capsid peak, the inventors determined an absorbance normalization $n_{A280/A50}$. By multiplying the A504 for the refilled capsid peak by n the inventors obtained the amount of A280 absorbance related to Cp150Bo. Thus, the fraction of Cp150Bo ($X_{Cp150Bo,capsid}$) in the refilled capsid peak is $$X_{Cp150Bo,capsid} = \left(A504_{refilled} \times n_{A280/A50}\right)/A280_{refilled} \qquad (1)$$

$$= (1.7 \times 0.579)/7.4$$

$$= 0.133$$

Cp150Bo accounted for ~13% of the absorbance of the refilled capsid peak. If all of these capsids were T=4 particles, this gives an average of ~16 Cp150Bo dimers per capsid. It agrees well with the RPS data and Cryo-EM data, showing a hole missing ~9 to 18 dimers. The presence of some homogeneous Cp150Bo capsids and some T=3 particles in the refilled holey capsid sample cannot be excluded. The majority of the BODIPY absorbance arose from the refilled Cp150Bo dimers.

These results demonstrate that holey capsids can react with free dimers, such as Cp150Bo. This result shows that other modified homodimers, potentially carrying moieties can be incorporated into the holey capsids through the reassembly process.

Experimental Example 8—Discussion

To create an asymmetric assembly pathway with asymmetric capsids requires a means to initiate assembly with a specific complex and a means of halting and possibly restarting assembly at a specific juncture. As an example, an asymmetric assembly pathway was designed, from asymmetric subunits to asymmetric holey capsids, and eventually to asymmetric T=4 capsids (FIG. 1). With this designed pathway, stages in the reaction were created, which yield opportunities for modifications and engineering.

To achieve asymmetric assembly in accordance with some embodiments, the 149-residue HBV capsid protein assembly domain, Cp149, was modified. A heterodimeric subunit was created—Cp149$_{His}$Cp149$_{Y132A}$ (FIG. 2A)—that possesses functionalities on each monomer, one encoding a programable assembly function and the other encoding a conditional stop. The assembly active monomer can assemble in response to ionic strength, like wildtype dimer, and is also sensitive to $Ni^{2+}$ due to the addition of a His-Tag. The conditional stop monomer carries the assembly-incompetent mutation Y132A, which inhibits assembly due to loss of hydrophobic surface for proper subunit interactions; however, it can still co-assemble with wildtype dimers into labile capsids.

In the engineered assembly path (FIG. 1), the asymmetric heterodimers assemble in response to $Ni^{2+}$ but will stop after forming an initial complex, a hexamer in this diagram, due to the influence of Y132A. Hexamers then can be used as nuclei to co-assemble with a second species of dimer, in response to high ionic strength. The resulting hybrid capsids have two distinct patches, the hexamer nucleus, and the homodimer component. To further manipulate the structure, patches were differentially stabilized, which can be accomplished by using a homodimer that can spontaneously form crosslinks. In some embodiments, Cp150 homodimers can be used. As a Cp149 variant, Cp150 incorporates a C-terminal cysteine that clusters at fivefold and quasi-sixfold vertices resulting in disulfide crosslinks. Crosslinked regions in hybrid capsids are stable under low ionic strength and urea treatment. Because the heterodimer lacks cysteine 150 and fails to crosslink, heterodimer patches can be removed specifically, leaving crosslinked asymmetric holey capsids. Such holey capsids then can be further modified, and/or the surface can be refilled with new subunits to generate symmetric or asymmetric, un-holey T=4 complete capsids.

Symmetric subunits often spontaneously assemble into symmetric capsids with no stops. Described now is a strategy to break the continuous HBV capsid assembly into a series of independent reactions. The key to this process is to design a heterodimer with distinct assembly properties programmed into each monomer. One monomer is assembly-active and can assemble in response to $Ni^{2+}$, whereas the other monomer is assembly-incompetent alone but can co-assemble with additional homodimers. By manipulating assembly conditions with the designed heterodimer, a set of independent assembly reactions can be achieved. The different reactions yielded: hexamer, asymmetric co-assembled capsids, asymmetric holey capsids, and surface-refilled asymmetric un-holey capsids. Formation of the asymmetric capsids mimics the assembly of bacteriophage P22, where a portal complex nucleates capsid assembly. However, in this case, the "hexamer portals" can be removed to create asymmetric holey capsids where the surface can be subsequently refilled with other engineered dimers. This process provides many opportunities to engineer asymmetric and symmetric capsids for a range of applications, e.g., loading cargos into holey capsids, attaching a chemistry to a small contiguous patch of dimers. A path for making very small, 36-nm diameter, Janus particles with molecular uniformity is thus provided.

Many viral capsids have subunits that can be asymmetrized, though it is easiest to see doing this with monomers and dimers. There are likely to be some fundamental requirements needed to thermodynamically separate the individual steps of the reactions. First, the self-assembly system must be reversible. Second, it must be possible to create an asymmetric subunit where at least one face is able to conditionally stop assembly under conditions where the other face assembles. In HBV, the Y132A mutation provided an additional barrier to assembly that might have proceeded once a nucleus is formed, even at low ionic strength. Third, it must be possible to overcome the conditional stop. In HBV, the inventors depended on the multivalent binding sites afforded by the hexameric nucleus and the relatively high association energy for subunit addition afforded by high ionic strength. Finally, there must be a substantial energy gradient between the nucleus and the growing capsid that can be manipulated to change which domain is more stable. In low ionic strength and moderate $Ni^{2+}$ concentration, the hexameric nucleus is more stable than capsid. After disulfide crosslinking and in the presence of EDTA and urea, the Cp150 capsid is far more stable than the hexamer. Engineering a crosslinkable His-tag and a crosslinkable cysteine into a location near a vertex provides one strategy. The use of elastin-like peptides in Cowpea Chlorotic mottle virus capsid protein as an example of a capsid with two modes of regulatable assembly[58].

Asymmetric capsids can figuratively and literally open a window to create organized, multi-functionalized particles.

An advantage of capsid-like particles is their ability to display clusters of an epitope or a receptor-binding tag; assembly of an asymmetric particle can create patches of two different ligands to take advantage of multivalent display and high-avidity binding. Asymmetry can be leveraged to create Janus particles that, for example, adsorb to each other to make supramolecular structures or adsorb to a surface to generate a molecular monolayer. A holey capsid is a unique structure that allows unique access to the sequestered interior of the particle as well as release of its contents providing flexibility for a capsid-like structures that have already been repurposed as a container for delivery or as vessel for chemistry.

---

The invention claimed is:

1. An orthohepadnavirus capsid protein (Cp) heterodimer, comprising
   i) a first half-dimer comprising an orthohepadnavirus Cp, and
   ii) a second half-dimer comprising an orthohepadnavirus Cp, wherein the first half-dimer and the second half-dimer are not identical, wherein the first half-dimer and the second half-dimer are not linked by a peptide linker,
   wherein the orthohepadnavirus Cp is hepatitis B virus (HBV) Cp,
   wherein the HBV Cp comprises an assembly domain (Cp149) comprising SEQ ID NO:8,
   wherein at least one of the first half-dimer and the second half-dimer has a capsid assembly defect,
   wherein the capsid assembly defect comprises the HBV Cp149 comprising at least one amino acid substitution in SEQ ID NO:8,
   wherein the substituted HBV Cp149 is selected from HBV Cp149-S106A, HBV Cp149-G123A, HBV Cp149-V124A, HBV Cp149-V124C, HBV Cp149-T128A, and HBV Cp149-Y132A, and
   wherein the first half-dimer and the second half-dimer spontaneously dimerize with one another.

2. The orthohepadnavirus Cp heterodimer of claim 1, wherein one of the first half-dimer and the second half-dimer comprises a polypeptide insertion within a spike region of the first half-dimer or the second half-dimer, the polypeptide insertion being selected from: an exogenous polypeptide epitope, an exogenous immunogenic polypeptide, an exogenous therapeutic polypeptide, an exogenous ligand polypeptide, a capsid self-assembly or disassembly regulating polypeptide sequence, and an exogenous catalytic polypeptide.

3. The orthohepadnavirus Cp heterodimer of claim 1, wherein one or both of the first half-dimer and the second half-dimer comprises a polypeptide linked to a C-terminus of the first half-dimer or second half-dimer, the linked polypeptide being selected from: a capsid self-assembly or disassembly regulating polypeptide sequence, an exogenous catalytic polypeptide, an exogenous affinity tag polypeptide, a C-terminal cysteine, an exogenous elastin-like polypeptide, an exogenous leucine zipper polypeptide, an exogenous catalytic polypeptide, or an exogenous fluorescent polypeptide.

4. The orthohepadnavirus Cp heterodimer of claim 1, wherein either the first half dimer or the second half-dimer comprises a polyhistidine tag or a histidine affinity tag.

5. The orthohepadnavirus Cp heterodimer of claim 1, wherein the first half-dimer comprises a first HBV Cp, and the second half-dimer comprises a second HBV Cp.

6. The orthohepadnavirus Cp heterodimer of claim 1, wherein the first half dimer comprises HBV Cp149, and the second half-dimer comprises HBV Cp149-Y132A.

7. A bicistronic vector encoding an orthohepadnavirus capsid protein (Cp) heterodimer according to claim 1.

8. A method for making an orthohepadnavirus capsid protein (Cp) heterodimer, comprising:
   a) introducing the bicistronic vector of claim 7 into a cell;
   b) incubating the cell comprising the bicistronic vector for a time sufficient for the cell to express the first half-dimer and the second-half dimer from the bicistronic vector; and
   c) recovering and purifying a heterodimer consisting of the first half-dimer and the second half-dimer.

9. A viral capsid protein hexamer comprising six orthohepadnavirus capsid protein (Cp) heterodimers according to claim 1.

10. The viral capsid protein hexamer of claim 9, wherein the first half-dimer or the second half dimer of each one of the six orthohepadnavirus Cp heterodimers comprises a polyhistidine tag, and the viral capsid hexamer further comprises metal ions selected from Ni2+, Co2+, Cu2+, and Zn2+.

11. A method for making a viral capsid protein hexamer, comprising incubating a plurality of orthohepadnavirus capsid protein (Cp) heterodimers according to claim 1 with metal ions selected from Ni2+, Co2+, Cu2+, and Zn2+in a low ionic strength buffer, wherein the first half-dimer or the second half-dimer of each heterodimer of the plurality of orthohepadnavirus Cp heterodimers comprises a polyhistidine tag.

12. A virus-like particle (VLP), comprising a plurality of orthohepadnavirus capsid protein (Cp) heterodimers according to claim 1.

13. The VLP of claim 12, further comprising a plurality of orthohepadnavirus Cp homodimers.

14. A method for making a virus-like particle (VLP), comprising incubating metal ions selected from Ni2+, Co2+, Cu2+, and Zn2+in a low ionic strength buffer with i) a plurality of orthohepadnavirus capsid protein (Cp) heterodimers according to claim 1, or ii) a combination of a plurality of orthohepadnavirus capsid protein (Cp) heterodimers according to claim 1 and a plurality of orthohepadnavirus homodimers.

15. The method of claim 14, wherein the plurality of orthohepadnavirus Cp heterodimers each comprise a different polypeptide insertion; or one of the one or more populations of orthohepadnavirus Cp heterodimers does not include a polypeptide insertion, and each additional population of orthohepadnavirus Cp heterodimers each comprise a different polypeptide insertion.

\* \* \* \* \*